(12) United States Patent
Castro et al.

(10) Patent No.: US 7,772,413 B2
(45) Date of Patent: Aug. 10, 2010

(54) AMIDE AND PEPTIDE DERIVATIVES OF TETRAALKYLENEPENTAMINES AS TRANSFECTION AGENTS

(75) Inventors: Mariano Javier Castro, Cambridge (GB); Christopher Kitson, Stevenage (GB); Mark Ladlow, Cambridge (GB); Alpesh Patel, Cambridge (GB)

(73) Assignee: Glaxo Group Limited, Brentford, Middlesex (GB)

( * ) Notice: Subject to any disclaimer, the term of this patent is extended or adjusted under 35 U.S.C. 154(b) by 648 days.

(21) Appl. No.: 11/719,440

(22) PCT Filed: Nov. 17, 2005

(86) PCT No.: PCT/EP2005/012461

§ 371 (c)(1),
(2), (4) Date: May 16, 2007

(87) PCT Pub. No.: WO2006/053783

PCT Pub. Date: May 26, 2006

(65) Prior Publication Data

US 2009/0149401 A1   Jun. 11, 2009

(30) Foreign Application Priority Data

Nov. 19, 2004   (GB) ................... 0425556.8

(51) Int. Cl.
    *C07C 233/05*   (2006.01)
(52) U.S. Cl. ........................... 554/37; 564/153
(58) Field of Classification Search .............. 564/153; 554/37
    See application file for complete search history.

(56) References Cited

U.S. PATENT DOCUMENTS

| | | | |
|---|---|---|---|
| 2,528,273 | A | 10/1950 | Gunderson et al. |
| 2,921,048 | A | 1/1960 | Bell et al. |
| 3,337,459 | A | 8/1967 | Ford |
| 3,438,898 | A | 4/1969 | Schlobohm et al. |
| 3,522,205 | A | 7/1970 | Gobran et al. |
| 3,888,775 | A | 6/1975 | Koizumi et al. |
| 4,551,505 | A | 11/1985 | Sauerbier et al. |
| 5,068,240 | A | 11/1991 | Kovacs et al. |
| 5,744,335 | A | 4/1998 | Wolfe et al. |
| 2004/0188047 | A1 | 9/2004 | Nakamura et al. |

FOREIGN PATENT DOCUMENTS

| | | |
|---|---|---|
| DE | 2515146 | 10/1976 |
| WO | WO9853127 | 11/1998 |
| WO | WO9905914 | 2/1999 |

OTHER PUBLICATIONS

Katritzky, et al: "Synthesis of Dendramines, dendramides and their New application in the oil industry." 1998: STN Database and Journal of the Chinese Chemical Society (Taipei), 44(6) 575-580 Coden: JCCTAC; ISSN: 0009-4536, 1997.
Harle, O.L.: "Inhibition of oxidation, II" Database accession No. 1961: 35038 abstract & American Chem. Soc., Div. Petrol. Chem., Preprints, 2(No. 1), 51-74, 1957.
Kishima, Noboru, et al.: "Curing of Epoxy resins with amides from polyethylenepolyamines and fatty acids", retrieved from STN Database accession No. 1989: 535398 Abstract & CA 1 246 817A1 (Toto, Ltd., Japan) Dec. 20, 1988.
Kwith, Hada: "Fatty acid amides as neoplasm inhibitors and their synthesis", retrieved from STN Database accession No. 1988:161429 abstract 7 CN 85 100 625 CN (Hung.) Jan. 1985.
Murahashi, Tomoyuki, et al: "Sizes for glass fibers", retrieved from STN Database accession No. 2001:873138 abstract & JP 2001 335345 A2 (Sanyo Chemical Industries, Ltd., Japan) Dec. 4, 2001.
Honjo, Shuichi, et al.: "Additives for powdered coal and oil mixtures", retrived from STN Database accession No. 1993:150818 abstract & JP 04 057889 A2 (Daichi Kogyo Seiyaku K. K., Japan) Feb. 25, 1992.
Nagao, Kazuki, et al.: "Wet-end additives for papermaking with reduced 1,3-dichloro-2propanol (DCP) byproduct contamination", retrieved from STN Database accession No. 2003:387075 abstract & JP 2003 147692A2 (Japan PMC Corp, Japan) May 21, 2003.
Sekimoto, Masanori, et al: "Diesel fuel compositions", retrieved from STN database accession No. 1987:579958 abstract & JP 62 086092A2 (Nippon Oil Co., Ltd., Japan) Apr. 20, 1987.
Nakamura, Yoshinobu et al: "Manufacture of metal powders for magnetic recording", retrieved from STn Database accession No. 1988:67600 abstract & JP 62 150529A2 (Toho Chemical Industry Co., Ltd., Japan) Jul. 4, 1987.
Nishimura, Takeo: "Age resistors for polyurethanes" retrieved from STN Database accession No. 1976:544053 abstract & JP 51 034947A2 (Kuraray Co., Ltd., Japan) Mar. 25, 1976.
Shiojiri, Eiji, et. al: "Electron beam-curable electrically conductive pastes and their use in printed circuit boards", retrived from STN Database accession No. 1994:669671 abstract & JP 06 157945A2 (Ajinomoto KK, Japan) Jun. 7, 1994.

*Primary Examiner*—Shailendra Kumar
(74) *Attorney, Agent, or Firm*—Reid S. Willis; John Lemanowicz

(57) ABSTRACT

The invention relates to newly identified pentamine based surfactant compounds, to the use of such compounds and their production. The invention also relates to the use of the pentamine based compounds to facilitate the transfer of polynucleotides into cells.

13 Claims, 10 Drawing Sheets

AMIDE AND PEPTIDE DERIVATIVES OF TETRAALKYLENEPENTAMINES AS TRANSFECTION AGENTS

This application is 371 of PCT/EP2005/012461, filed Nov. 17, 2005.

This invention relates to newly identified pentamine based surfactant compounds, to the use of such compounds and to their production. The invention also relates to the use of the pentamine based compounds to facilitate the transfer of polynucleotides into cells and also to facilitate the transfer of therapeutically active compounds into cells for drug delivery. Compounds with properties related to properties of compounds of the invention are often referred to as Gemini surfactants.

Surfactants are substances that markedly affect the surface properties of a liquid, even at low concentrations. For example surfactants will significantly reduce surface tension when dissolved in water or aqueous solutions and will reduce interfacial tension between two liquids or a liquid and a solid. This property of surfactant molecules has been widely exploited in industry, particularly in the detergent and oil industries. In the 1970s a new class of surfactant molecule was reported, characterised by two hydrophobic chains with polar heads which are linked by a hydrophobic bridge (Deinega, Y et al., *Kolloidn. Zh.* 36, 649, 1974). These molecules, which have been termed "gemini" (Menger, F M and Littau, C A, *J. Am. Chem. Soc.* 113, 1451, 1991), have very desirable properties over their monomeric equivalents. For example they are highly effective in reducing interfacial tension between oil and water based liquids and have a very low critical micelle concentration (Menger, F M and Keiper, J S, *Angewandte. Chem. Int. Ed. Engl.,* 2000, 39, 1906).

Cationic surfactants have been used inter alia for the transfection of polynucleotides into cells in culture, and there are examples of such agents available commercially to scientists involved in genetic technologies (for example the reagent Tfx™-50 for the transfection of eukaryotic cells available from Promega Corp. Wis., USA).

The efficient delivery of DNA to cells in vivo, either for gene therapy or for antisense therapy, has been a major goal for some years. Much attention has concentrated on the use of viruses as delivery vehicles, for example adenoviruses for epithelial cells in the respiratory tract with a view to corrective gene therapy for cystic fibrosis (CF). However, despite some evidence of successful gene transfer in CF patients, the adenovirus route remains problematic due to inflammatory side-effects and limited transient expression of the transferred gene. Several alternative methods for in vivo gene delivery have been investigated, including studies using cationic surfactants. Gao, X et al. *Gene Ther.* 2, 710-722, 1995 demonstrated the feasibility of this approach with a normal human gene for CF transmembrane conductance regulator (CFTR) into the respiratory epithelium of CF mice using amine carrying cationic lipids. This group followed up with a liposomal CF gene therapy trial which, although only partially successful, demonstrated the potential for this approach in humans (Caplen, N J. et al., *Nature Medicine*, 1, 39-46, 1995). More recently other groups have investigated the potential of other cationic lipids for gene delivery (Miller, A, *Angew. Int. Ed. Engl.,* 37, 1768-1785, 1998), for example cholesterol derivatives (Oudrhiri, N et al. *Proc. Natl. Acad. Sci.* 94, 1651-1656, 1997). This limited study demonstrated the ability of these cholesterol based compounds to facilitate the transfer of genes into epithelial cells both in vitro and in vivo, thereby lending support to the validity of this general approach.

The use of non-viral (cationic lipid) vectors for gene transfection has recently been reviewed, see D. Niculescu-Duvaz, J. Heyes and C. J. Springer, *Curr. Med. Chem.,* 2003, 10, 1233.

These studies, and others, show that in this new field of research there is a continuing need to develop novel low-toxicity surfactant molecules to facilitate the effective transfer of polynucleotides into cells both in vitro for transfection in cell-based experimentation and in vivo for gene therapy and antisense treatments. Gemini surfactants based on cysteine (WO99/29712) or on spermine (WO00/77032) or diamine (WO00/76954) have previously been made. Other examples of gemini surfactants are found in WO00/27795, WO02/30957, WO02/50100 and WO 03/82809. The use of Gemini surfactants as polynucleotide vectors has recently been reviewed (A. J. Kirby, P. Camilleri, J. B. F. N. Engberts, M. C. Feiters, R. J. M. Nolte, O. Söderman, M. Bergsma, P. C. Bell, M. L. Fielden, C. L. Garcia Rodriguez, Philippe Guédat, A. Kremer, C. McGregor, C. Perrin, G. Ronsin and M. C. P. van Eijk, *Angew. Chem. Int. Ed.,* 2003, 42, 1448, see also R. Zana and J. Xia, *Gemini Surfactants,* Marcel Dekker, NY, 2004)

A recently developed technique involves the use of synthetic short interfering (si) double stranded RNA molecules to transiently suppress gene function. This technique of RNA interference (RNAi), originally coined from work in *C. elegans* (A. Fire, Trends Genet., 1999, 15 (9), 358) was later developed such that its use could be applied to mammalian cells (S. M. Elbashir, J. Harborth, W. Lendeckel, A. Yalcin, K. Weber, T. Tuschl, Nature, 2001, 411, 494). The ability to deliver these siRNA effector molecules to the correct location of the majority of a cell population is a key step in the effective utilisation of this technology. Once correctly localised the antisense strand of the RNA duplex binds to the complementary region of the targeted messenger (m)RNA (coding for the target of interest), leading to hydrolysis of the mRNA and its subsequent degradation. This transient reduction in mRNA leads to a transient reduction in target gene expression. Highly efficient delivery and correct localisation are required to reduce target gene expression to levels such that the function of the target can be elucidated.

The present invention seeks to overcome the difficulties exhibited by existing compounds.

The invention relates to compounds having the general structure of formula (I):

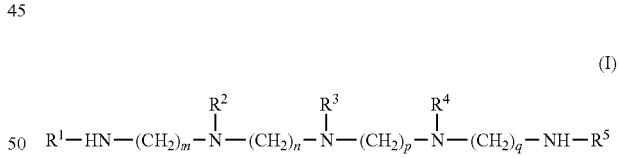

wherein
m is 1 to 6;
q is 1 to 6;
n is 1 to 10;
p is 1 to 10;
$R^1$, $R^2$, $R^3$, $R^4$ and $R^5$, which may be the same or different, is each selected from hydrogen, $R^w$, or $(Aa)_x$;
where $R^w$ is a saturated or unsaturated, branched or unbranched aliphatic carboxylic acid of up to 24 carbon atoms linked as its amide derivative, and wherein at least two $R^w$ groups are present in the molecule;
$(Aa)_x$, which may be the same or different at each occurrence, is a series of x natural or unnatural amino acids linked in a linear or branched manner;
x is 0 to 6.

or a salt, preferably a pharmaceutically acceptable salt thereof.

Preferably m is 2 or 3, most preferably 3.
Preferably q is 2 or 3, most preferably 3.
Preferably n is 3 to 6, most preferably 4.
Preferably p is 3 to 6, most preferably 3.

(Aa) is preferably a basic amino acid. Examples of basic amino acids include [$H_2N(CH_2)_3$]$_2N(CH_2)CO_2H$, ($H_2NCH_2$)$_2CHCO_2H$, or L or D enantiomers of Ser, Lys, Orn, Dab (Diamino butyric acid) or Dap (diamino propionic acid). For example, the amino acid (Aa) may be an amino acid comprising an amino group (or optionally an OH group) in its side chain and comprising not more that 12 carbon atoms in total, for example not more that 10 carbon atoms in total.

x is preferably 1 to 4. Most preferably, x is 1.

In one embodiment a), $R^1$ and $R^5$ are both $R^w$, and $R^2$, $R^3$ and $R^4$ are all $(Aa)_x$:

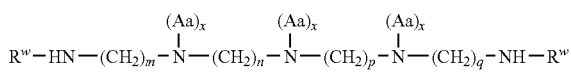

where $R^1$ and $R^5$ are independently $R^w$ as defined above and $R^2$, $R^3$ and $R^4$ are independently $(Aa)_x$ as defined above. In such an embodiment, $R^1$ and $R^5$ may, for example be the same $R^w$ and $R^2$, $R^3$ and $R^4$ may, for example be the same $(Aa)_x$.

In another embodiment b), $R^2$ and $R^4$ are $R^w$, $R^3$ is hydrogen and $R^1$ and $R^5$ are $(Aa)_x$:

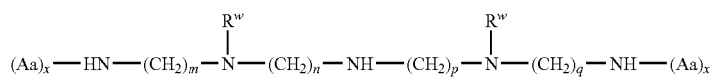

where $R^2$ and $R^4$ are independently $R^w$ as defined above and $R^1$ and $R^5$ are independently $(Aa)_x$ as defined above. In such an embodiment, $R^2$ and $R^4$ may, for example be the same $R^w$ and $R^1$ and $R^5$ may, for example be the same $(Aa)_x$.

In another embodiment c), $R^2$ and $R^4$ are $R^w$, and $R^1$, $R^3$ and $R^5$ are all hydrogen or all $(Aa)_x$:

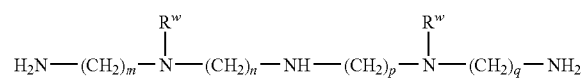

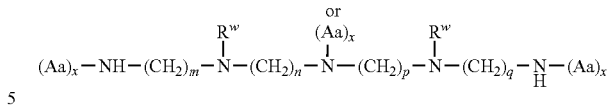

where $R^2$ and $R^4$ are independently $R^w$ as defined above and $R^1$, $R^3$ and $R^5$ are all H or all independently $(Aa)_x$ as defined above. In such an embodiment, $R^2$ and $R^4$ may, for example be the same $R^w$. $R^1$, $R^3$ and $R^5$ may, for example be the same (Aa).

In another embodiment d), $R^2$, $R^3$ and $R^4$ are $R^w$; and $R^1$ and $R^5$ are both hydrogen or both $(Aa)_x$.

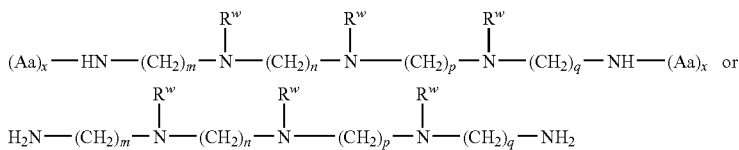

where $R^2$, $R^3$ and $R^4$ are $R^w$ and $R^1$ and $R^5$ are both hydrogen or both $(Aa)_x$ as defined above. In such an embodiment, $R^2$, $R^3$ and $R^4$ may, for example be the same $R^w$ and $R^1$ and $R^5$ may, for example be the same $(Aa)_x$.

In a further preferred embodiment the $R^w$ saturated or unsaturated, branched or unbranched aliphatic carboxylic acid of up to 24 carbon atoms linked as its amide derivative has 10 or more carbon atoms, for example 12 or more, for example 14 or more, for example 16 or more carbon atoms. In a further preferred embodiment the $R^w$ saturated or unsaturated, branched or unbranched aliphatic carboxylic acid of up to 24 carbon atoms linked as its amide derivative is selected from:

—C(O)(CH$_2$)$_{10}$CH$_3$
—C(O)(CH$_2$)$_{12}$CH$_3$
—C(O)(CH$_2$)$_{14}$CH$_3$
—C(O)(CH$_2$)$_{16}$CH$_3$
—C(O)(CH$_2$)$_{18}$CH$_3$
—C(O)(CH$_2$)$_{20}$CH$_3$
—C(O)(CH$_2$)$_7$CH═CH(CH$_2$)$_5$CH$_3$ natural mixture
—C(O)(CH$_2$)$_7$CH═CH(CH$_2$)$_7$CH$_3$ natural mixture
—C(O)(CH$_2$)$_7$CH═CH(CH$_2$)$_5$CH$_3$ Cis
—C(O)(CH$_2$)$_7$CH═CH(CH$_2$)$_7$CH$_3$ Cis
—C(O)(CH$_2$)$_7$CH═CH(CH$_2$)$_5$CH$_3$ Trans
—C(O)(CH$_2$)$_7$CH═CH(CH$_2$)$_7$CH$_3$ Trans
—C(O)(CH$_2$)$_7$CH═CHCH$_2$CH═CH(CH$_2$)$_4$CH$_3$
—C(O)(CH$_2$)$_7$(CH═CHCH$_2$)$_3$CH$_3$
—C(O)(CH$_2$)$_3$CH═CH(CH$_2$CH═CH)$_3$(CH$_2$)$_4$CH$_3$
—C(O)(CH$_2$)$_7$CHCH(CH$_2$)$_7$CH$_3$
—C(O)CH$_2$CH(CH$_3$)[CH$_2$CH$_2$CH$_2$CH(CH$_3$)]$_3$CH$_3$
or —C(O)(CH$_2$)$_{22}$CH$_3$.

Most preferably the group is selected from —CO(CH$_2$)$_7$CH═CH(CH$_2$)$_7$CH$_3$ natural mixture, —CO(CH$_2$)$_7$CH═CH(CH$_2$)$_7$CH$_3$ Cis and —CO(CH$_2$)$_7$CH═CH(CH$_2$)$_7$CH$_3$ Trans.

In one embodiment, a compound of the invention is a so-called 'Gemini' surfactant compound. That is to say that the compound is symmetrical with at least two aliphatic chains.

Compounds of the present invention may be prepared from readily available starting materials using synthetic chemistry well known to the skilled person. The scheme shown in FIG. 1 shows a general scheme for the synthesis of an intermediate 5 for the synthesis of compounds of the invention.

As shown in the general scheme of FIG. 2, the intermediate 5 may be protected and reduced to give advanced pentamine intermediate 7 in which the $R^2$, $R^3$ and $R^4$ positions are protected and the $R^1$ and $R^5$ positions are free $NH_2$ groups. By further reaction of the amino groups at $R^1$ and $R^5$ positions to add $R^w$ groups, and deprotection of the $R^2$, $R^3$ and $R^4$ positions followed by addition of $(Aa)_x$ groups under appropriate conditions, molecules with the substitution pattern according to embodiment a) of the invention may be made.

As shown in the general scheme of FIG. 4, the intermediate 5 may be reduced to give a different advanced pentamine intermediate 12 in which only the $R^3$ position is protected and the $R^1$, $R^2$, $R^4$ and $R^5$ positions are free amino groups. By subsequent protection of the primary amino groups at $R^1$ and $R^5$ positions and addition of $R^w$ groups at the $R^2$ and $R^4$ positions followed by deprotection at $R^1$ and $R^5$ and addition of $(Aa)_x$ groups under appropriate conditions, and final deprotection at the $R^3$ position molecules with the substitution pattern according to embodiment b) of the invention may be made. If the addition of groups $(Aa)_x$ groups at the $R^1$ and $R^5$ positions is omitted, molecules with the substitution pattern according to embodiment c) of the invention may be made in analogous fashion. If the deprotection at the $R^5$ position occurs before addition of the $(Aa)_x$ groups, molecules with the substitution pattern according to the second alternative of embodiment c) of the invention may be made in analogous fashion.

As shown in the general scheme of FIG. 5, the advanced intermediate 13, which may be made from intermediate 12, and which is protected at the $R^1$, $R^3$ and $R^5$ positions may be deprotected at the $R^3$ position and subsequently functionalised by addition of an $R^w$ group to each of the $R^2$, $R^3$ and $R^4$ positions. By subsequent deprotection of the amino groups at $R^1$ and $R^5$ positions and addition of $(Aa)_x$ groups under appropriate conditions, and final deprotection, molecules with the substitution pattern according to embodiment d) of the invention may be made. If the addition of groups $(Aa)_x$ groups at the $R^1$ and $R^5$ positions is omitted, molecules with the substitution pattern according to the alternative of embodiment d) of the invention with primary amino groups at the $R^1$ and $R^5$ positions may be made in analogous fashion.

Various alternative protection and deprotection strategies are well known to the skilled person and suitable strategies may be devised for any particular desired final substitution pattern. For unsymmetric substitution patterns, physical separation of products or intermediates may be necessary. Suitable separation methods, for example chromatographic methods, are well known to the person skilled in the art.

Salts of molecules in accordance with the invention may be prepared by standard techniques, as shown for example in the schemes in FIGS. 6 and 7. In the scheme shown in FIG. 6, the salt formation step is also a deprotection step.

Another aspect of the invention relates to methods for using the pentamine based compounds. Such uses include facilitating the transfer of oligonucleotides and polynucleotides into cells for antisense, gene therapy and genetic immunisation (for the generation of antibodies) in whole organisms. Other uses include employing the compounds of the invention to facilitate the transfection of polynucleotides into cells in culture when such transfer is required, in, for example, gene expression studies and antisense control experiments among others. Protocols for the preparation of such polynucleotides and antisense molecules are well known in the art (for example Sambrook et al., Molecular Cloning: A Laboratory Manual, 2nd Ed., Cold Spring Harbor Laboratory Press, Cold Spring Harbor, N.Y. (1989), Cohen, J S ed. Oligodeoxynucleotides as Antisense Inhibitors of Gene Expression, CRC Press, Boca Raton, Fla. (1989)). The polynucleotides can be mixed with the compounds, added to the cells and incubated to allow polynucleotide uptake. After further incubation the cells can be assayed for the phenotypic trait afforded by the transfected DNA, or the levels of mRNA expressed from said DNA can be determined by Northern blotting or by using PCR-based quantitation methods for example the Taqman® method (Perkin Elmer, Conn., USA). Compounds of the invention offer a significant improvement, typically between 3 and 6 fold, in the efficiency of cellular uptake of DNA in cells in culture, compared with compounds in the previous art. In the transfection protocol, the pentamine surfactant compound may be used in combination with one or more supplements to increase the efficiency of transfection. Such supplements may be selected from, for example:

(i) a neutral carrier, for example dioleyl phosphatidylethanolamine (DOPE) (Farhood, H., et al (1985) *Biochim. Biophys. Acta,* 1235-1289);

(ii) a complexing reagent, for example the commercially available PLUS reagent (Life Technologies Inc. Maryland, USA) or peptides, such as polylysine or polyornithine peptides or peptides comprising primarily, but not exclusively, basic amino acids such as lysine, ornithine and/or arginine (see for example Henner, W D et al (1973) J. Virol. 12 (4) pp 741-747). The list above is not intended to be exhaustive and other supplements that increase the efficiency of transfection are taken to fall within the scope of the invention.

In still another aspect, the invention relates to the transfer of genetic material in gene therapy using the compounds of the invention. For example the skilled person can develop gene delivery methodologies for use in gene therapy, involving the use of pentamine surfactant compounds of the present invention, using protocols that are well known in the art. For example the use of surfactants for delivery of gene transfer vectors to the lung is reviewed in Weiss, D J (2002) Molecular Therapy 6 (2) pp 148 to 152.

Yet another aspect of the invention relates to methods to effect the delivery of non-nucleotide based drug compounds into cells in vitro and in vivo using the compounds of the invention.

The following definitions are provided to facilitate understanding of certain terms used frequently herein.

"Amino acid" refers to dipolar ions (zwitterions) of the form $^+H_3NCH(R)CO_2^-$. They are differentiated by the nature of the group R, and when R is different from hydrogen can also be asymmetric, forming D and L families. There are 20 naturally occurring amino acids where the R group can be, for example, non-polar (e.g. alanine, leucine, phenylalanine) or polar (e.g. glutamic acid, histidine, arginine and lysine). In the case of un-natural amino acids R can be any other group which is not found in the amino acids found in nature.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNA's or RNA's containing one or more modified bases and DNA's or RNA's with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Transfection" refers to the introduction of polynucleotides into cells in culture using methods involving the modification of the cell membrane either by chemical or physical means. Such methods are described in, for example, Sambrook et al., *MOLECULAR CLONING: A LABORATORY MANUAL*, 2nd Ed., Cold Spring Harbor Laboratory Press, Cold Spring Harbor, N.Y. (1989). The polynucleotides may be linear or circular, single-stranded or double-stranded and may include elements controlling replication of the polynucleotide or expression of homologous or heterologous genes which may comprise part of the polynucleotide.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, trifluoroacetic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, trifluoroacetate, benzenesulfonate, methanesulfonate, ethanesulfonate, naphthalenesulfonate (e.g. 2-naphthalenesulfonate) or hexanoate salt.

The invention includes within its scope all possible stoichiometric and non-stoichiometric forms of the salts of the compounds of formula (I) including hydrates and solvates.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The invention will now be described by way of the following examples. The examples are not to be taken in any way to limit the scope of the invention.

EXAMPLES

Description 1: $N^1N^8$-Bis(trifluoroacetyl)-spermidine trifluoroacetate trifluoroacetic acid salt (2; m=3, n=4)

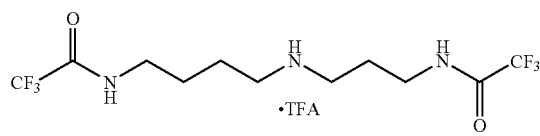

To a solution of spermidine 1 (m=3, n=4; 8.0 g, 55.0 mmol) in $CH_3CN$ (150 mL) and water (2.0 mL) was added ethyl trifluoroacetate (33.0 mL, 275 mmol) and the mixture was heated at reflux for 3 h. After cooling to room temperature, the solvent evaporated in vacuo. The residual solid was triturated with $CH_2Cl_2$ (2×150 mL) to afford the trifluoroacetic acid salt 2 as a white solid (21.0 g).

LC-MS (SI): $t_R$=1.10 min (m/z=338.1 [M+H]$^+$).

Description 2: $N^4$-(tert-Butoxycarbonyl)-$N^1$,$N^8$-bis(trifluoroacetyl)-spermidine (3; m=3, n=4)

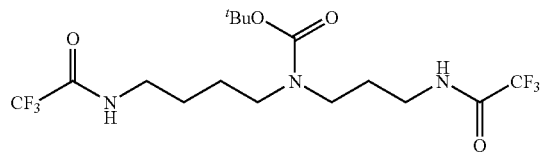

A solution of di-tert-butyl dicarbonate (11.3 g, 51.3 mmol) and triethylamine (75.0 mL, 54.0 mmol) in THF (25 mL) were added to $N^1$,$N^8$-bis(trifluoroacetyl)spermidine trifluoroacetate 2 (21.0 g, 46.7 mmol) under a nitrogen atmosphere. After 18 h at rt., the solvent was evaporated in vacuo and EtOAc (500 mL) was added. The solution was washed successively with 5% aqueous $NaHCO_3$ (2×150 mL) and brine (150 mL), dried ($Na_2SO_4$), and evaporated in vacuo to leave the Boc carbamate 3 as white solid (20.0 g).

LC-MS (ESI): $t_R$=4.09 min (m/z=438.3 [M+H]$^+$).

Description 3: $N^4$-(tert-Butoxycarbonyl)-spermidine (4; m=3, n=4)

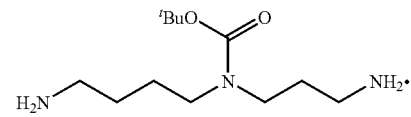

Aqueous sodium hydroxide solution (100 mL×0.5N) was added at 10° C. to a stirring solution of $N^4$-(tert-butoxycarbonyl)-N$^1$,N$^8$-bis(trifluoroacetyl)-spermidine 3 (20.0 g, 45.7 mmol) in MeOH (500 mL). The cooling bath was removed and the mixture was stirred for 18 h before the MeOH was evaporated in vacuo. The resulting aqueous suspension was extracted with [9:1] CHCl$_3$—MeOH (5×300 mL), and the combined organic extracts were dried (Na$_2$SO$_4$), and evaporated in vacuo to leave the Boc carbamate 4 as a colourless oil (10.0 g).

LC-MS (ESI): t$_R$=2.15 min (m/z=246.2 [M+H]$^+$).

Description 4: [4-(2-Cyano-ethylamino)-butyl]-[3-(2-cyano-ethylamino)-propyl]-carbamic Acid tert-butyl ester (5; m=3, n=4)

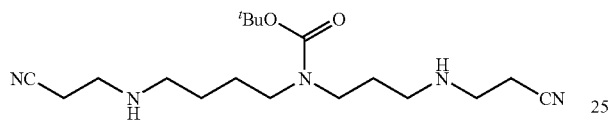

Acrylonitrile (2.15 mL, 32.6 mmol) was slowly added over 2 h to a stirring solution of the Boc carbamate 4 (4.0 g, 16.3 mmol) in MeOH (50 mL) maintained at 0° C. The resulting mixture was maintained at room temperature for a further 18 h and then concentrated in vacuo. The residue obtained was purified by column chromatograpghy (silica gel) eluting with MeOH:EtOAc [10:90] to give the bis-nitrile 5 as a colourless viscous oil (5.00 g).

LC-MS (ESI): t$_R$=2.15 min (m/z=352.1 [M+H]$^+$).

Description 5: {4-[tert-Butoxycarbonyl-(2-cyano-ethyl)-amino]-butyl}-{3-[tert-butoxycarbonyl-(2-cyano-ethyl)-amino]-propyl}-carbamic acid tert-butyl ester (6; m=3, n=4)

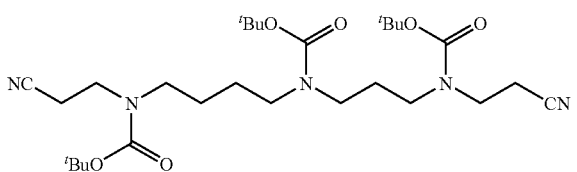

A solution of di-tert-butyl dicarbonate (3.40 g, 15.64 mmol) in THF (15 mL) was added to a solution of bis-nitrile 5 (2.5 g, 7.11 mmol) in a mixture of THF (10 mL) and triethylamine (15 mL) under a nitrogen atmosphere. After 18 h at room temperature, the solvent was evaporated in vacuo and EtOAc (100 mL) was added. The organic solution was washed successively with 5% aqueous NaHCO$_3$ solution (2×50 mL) and brine (50 mL), dried (Na$_2$SO$_4$), and evaporated in vacuo to afford the tris-Boc carbamate 6 as pale yellow liquid (3.9 g).

$^1$H-NMR (CDCl$_3$): δ$_H$ 1.45 (m, 31H), 1.75 (m, 2H), 2.60 (m, 4H), 3.16 (m, 4H), 3.26 (m, 4H), 3.45 (m, 4H).

Description 6: {4-[(3-Amino-propyl)-tert-butoxycarbonyl-amino]-butyl}-{3-[(3-amino-propyl)-tert-butoxycarbonyl-amino]-propyl}-carbamic acid tert-butyl ester (7; m=3, n=4)

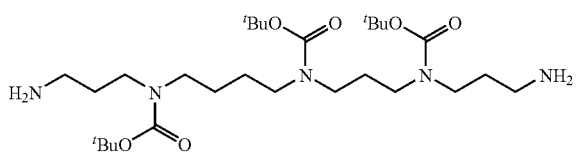

A mixture of tris-Boc nitrile 6 (3.90 g, 7.06 mmol), NaOH (0.45 g, 11.2 mmol) and Raney Nickel (2.1 g) in 95% ethyl alcohol (30 mL) was stirred at room temperature under a hydrogen atmosphere (1 atmos.) for 18 h. The catalyst was removed by filtration and the filtrate was concentrated in vacuo to 10 mL and treated with 40% aqueous NaOH solution (20 mL) and MeOH (10 mL). An oil separated which was extracted with CHCl$_3$ (2×100 mL). The combined organic extracts were dried (Na$_2$SO$_4$) and concentrated in vacuo to leave the diamine 7 as a pale yellow oil (3.90 g).

$^1$H-NMR (CDCl3): δ$_H$ 1.45 (brs, 31H), 1.63 (m, 4H), 1.73 (m, 2H), 2.67 (m, 4H), 3.20 (m, 12H).

Description 7: Octadec-9-enoic acid (3-amino-propyl)-(4-{3-[(3-amino-propyl)octadec-9-enoyl-amino]-propylamino}-butyl)-amide tris-trifluoroacetic acid salt (9; R=oleyl, m=3, n=4)

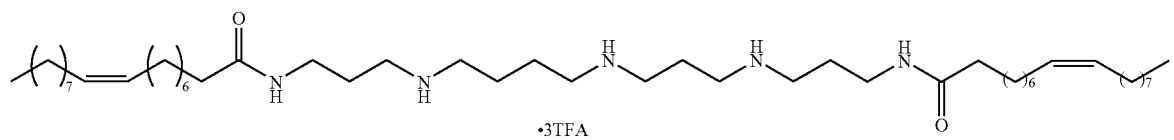

·3TFA

A solution of oleic acid N-hydroxysuccinimide ester (2.78 g, 7.32 mmol) in THF (50 mL) and a solution of potassium carbonate (1.08 g, 7.86 mmol) in water (10 mL) were added to a solution of 7 (632 mg, 2.58 mmol) in THF (40 mL). The resulting mixture was stirred at room temperature for 18 h and then concentrated in vacuo. The residue was dissolved in ethyl acetate (300 mL), washed with water (150 mL×2) then dried ($Na_2SO_4$) and concentrated in vacuo to leave the tris-Boc carbamate 8 as a colourless, viscous oil. The oil was dissolved in $CH_2Cl_2$ (25 mL) and treated with trifluoroacetic acid (15 mL). The resulting mixture was stirred at room temperature for 2 h, then concentrated in vacuo and the residue co-evaporated with diethyl ether (200 mL) to afford the tris-trifluoroacetic salt 9 as a white solid (3.72 g).

LC-MS (ESI): $t_R$=3.94 min (m/z=788.7 $[M+H]^+$).

Description 8: General Procedure to Prepare $N^1,N^8$-Dioleyl-$N^4$-tris-$(Aa)_x$-pentamine hydrochloride salts (11; R=oleyl, m=3, n=4)

The N-terminal-protected amino acid ($(PG)_y(Aa)_x$: 3.5 mol eq.) TBTU (298 mg, 0.93 mmol), HOBt (125 mg, 0.93 mmol) and diisopropylethylamine (0.20 g 1.59 mmol) were added to a solution of tris-amine 9 (300 mg, 0.27 mmol) in $CH_2Cl_2$ (15 mL). After stirring at room temperature for 18 h, the reaction mixture was concentrated in vacuo and the residue was dissolved in EtOAc (10 mL). The organic solution was washed with water (2×10 mL), dried ($Na_2SO_4$), and concentrated in vacuo to leave an oil that was purified by column chromatography (silica gel) eluting with MeOH:$CH_2Cl_2$ [5:95] to afford the intermediate Boc carbamate 10 as an oil. The carbamate 10 was dissolved in diethyl ether (2 mL) and treated with a solution of HCl in dioxane (4M, 4 mL). After stirring at room temperature for 18 h, the resulting white precipitate was collected by filtration, washed with anhydrous diethyl ether and

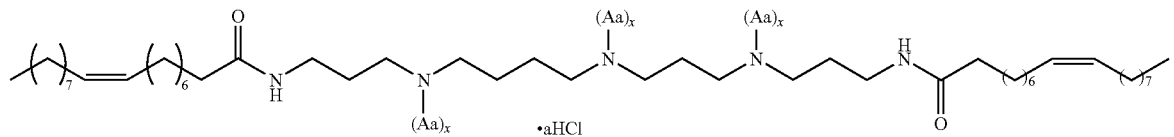

dried in vacuo to afford the pentamine hydrochloride salt 11 as a white powder (11-77%).

Example 1

$(Aa)_x$=L-Lys

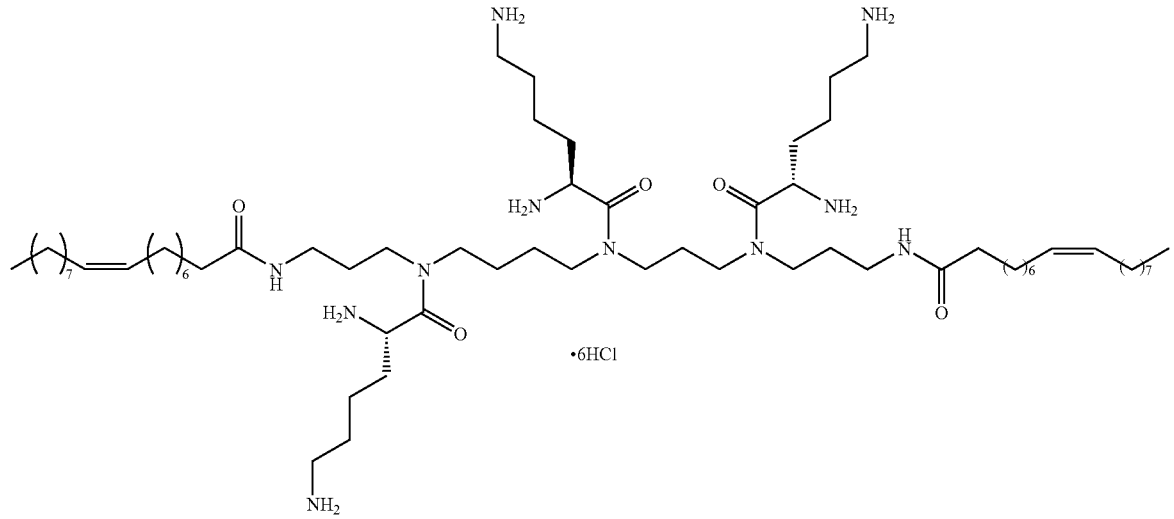

LC-MS (ESI): $t_R$=10.97 min (m/z=1173.1 [M+H]$^+$); HRMS (ESI) m/z calcd ($C_{67}H_{134}N_{11}O_5$) 1173.0569, found 1173.0542 [M+H]$^+$.
Example 2
$(Aa)_x$=D-Lys
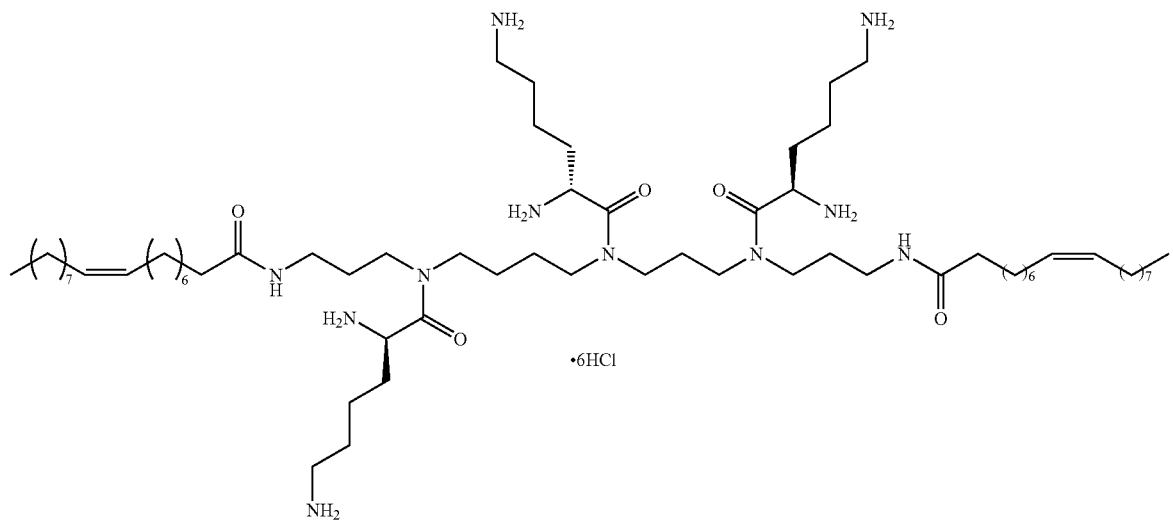
LC-MS (ESI): $t_R$=10.93 min (m/z=1173.1 [M+H]$^+$); HRMS (ESI) m/z calcd ($C_{67}H_{134}N_{11}O_5$) 1173.0569, found 1173.0540 [M+H]$^+$.
Example 3
$(Aa)_x$=L-Orn
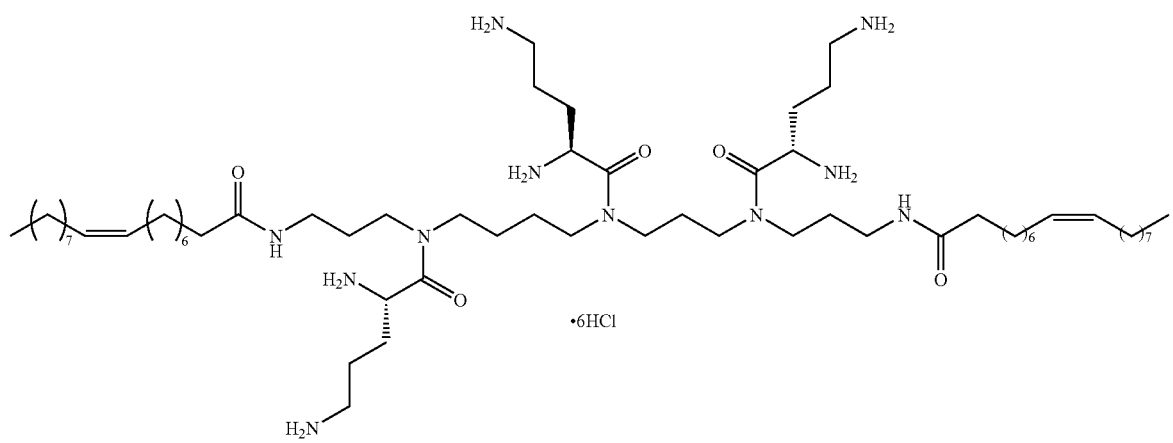

LC-MS (ESI): $t_R$=11.12 min (m/z=1131.0 [M+H]$^+$); HRMS (ESI) m/z calcd ($C_{64}H_{128}N_{11}O_5$) 1131.0100, found 1131.0087 [M+H]$^+$.

Example 4

$(Aa)_x$=L-Ser

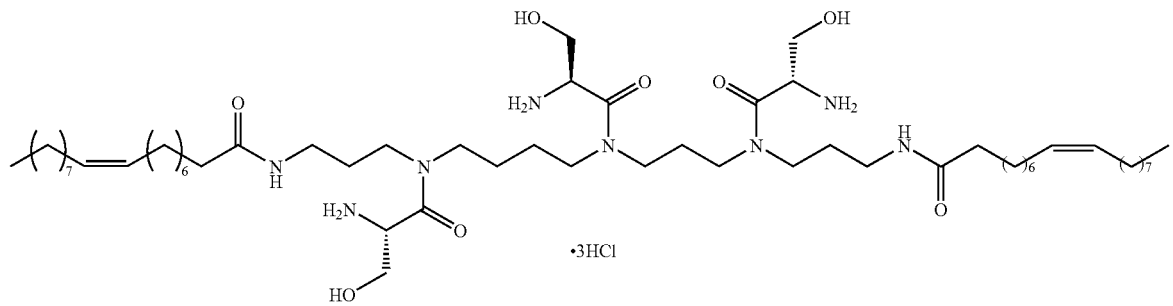

$^1$H-NMR (MeOH): $\delta_H$ 1.42-1.61 (m, 13H), 1.62-1.80 (m, 6H), 2.52-2.75 (m, 12H), 3.18-3.33 (m, 4H).

Description 10: {4-[3-(2,2,2-Trifluoro-acetylamino)-propylamino]-butyl}-{3-[3-(2,2,2-trifluoro-acetylamino)-propylamino]-propyl}-carbamic acid tert-butyl ester (13; m=3, n=4)

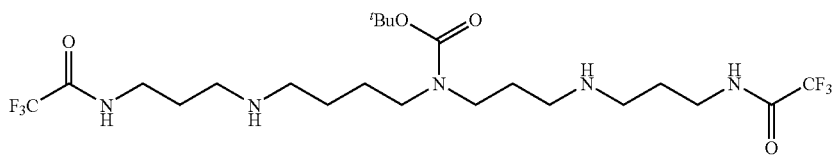

LC-MS (ESI): $t_R$=12.94 min (m/z=1049.9) [M+H]$^+$); HRMS (ESI) m/z calcd ($C_{58}H_{113}N_8O_8$) 1049.8681, found 1049.8662 [M+H]$^+$.

Description 9: [4-(3-Amino-propylamino)-butyl]-[3-(3-amino-propylamino)-propyl]-carbamic acid tert-butyl ester (12; m=3, n=4)

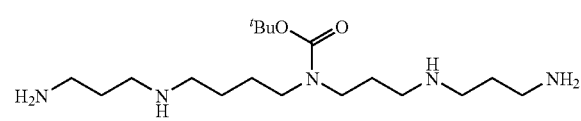

A mixture of the bis-nitrile 5 (3.10 g, 8.81 mmol), NaOH (0.3 g, 7.5 mmol) and Raney Nickel (1.5 g) in 95% ethyl alcohol (30 mL) was stirred at room temperature under a hydrogen atmosphere (1 atmos.) for 18 h. The catalyst was removed by filtration and the filtrate was concentrated in vacuo to 10 mL and treated with 40% aqueous NaOH solution (20 mL) and MeOH (10 mL). An oil separated which was extracted with CHCl$_3$ (2×100 mL). The combined organic extracts were dried (Na$_2$SO$_4$) and concentrated in vacuo to leave the amine 12 as a pale yellow oil (2.90 g).

To a solution of the amine 12 (2.98 g, 8.23 mmol) in CH$_3$CN (100 mL) was added ethyl trifluoroacetate (5.88 mL, 49.39 mmol) and water (2.0 mL). The reaction mixture was heated at reflux for 3 h, then allowed to cool to room temperature and the solvent evaporated in vacuo. The residual solid was triturated first with CH$_2$Cl$_2$ (50 mL) and then with anhydrous diethyl ether (100 mL) to afford the bis-trifluoroacetic acid salt 13 as a pale yellow solid (6.0 g).

$^1$H-NMR (DMSO): $\delta_H$ 1.35 (s, 9H), 1.45 (m, 4H), 1.78 (m, 6H), 2.88 (m, 8H), 3.07-3.19 (m, 4H), 3.25 (m, 4H), 8.48 (brs, 4H), 9.50 (m, 2H).

Description 11: {4-[(3-Amino-propyl)-octadec-9-enoyl-amino]-butyl}-{3-[(3-amino-propyl)-octadec-9-enoyl-amino]-propyl}-carbamic acid tert-butyl ester (15; m=3, n=4)

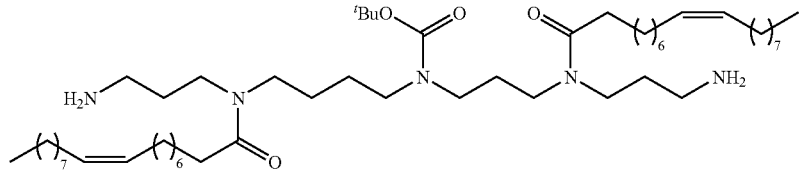

To a solution of oleic acid (1.60 g, 5.66 mmol) and the diamine 13 (2.00 g 2.57 mmol) in a mixture of $CH_2Cl_2$ (40 mL) and DMF (10 mL) were added TBTU (1.81 g, 5.66 mmol), HOBt (0.76 g, 5.66 mmol) and DIEA (1.99 g 15.42 mmol). After stirring at room temperature for 18 h, the reaction mixture was concentrated in vacuo. The residue was re-dissolved in $CH_2Cl_2$ (100 mL) and washed with 5% aqueous $KHSO_4$ (25 mL), 5% aqueous $K_2CO_3$ (2×25 mL) and brine (50 mL). The organic solution was dried ($Na_2SO_4$) and concentrated in vacuo to leave a gum that was purified by column chromatography (silica gel) eluting with a mixture of MeOH and $CHCl_3$ [3:97] to afford the intermediate trifluoroacetate 14 as a colourless gum. The gum was dissolved in MeOH (10 mL) and water (2 mL) and $K_2CO_3$ (1.13 g, 8.12 mmol) were added. The resulting mixture was stirred at room temperature for 18 h, then concentrated in vacuo. The residue was dissolved in $CH_2Cl_2$ (100 mL) and washed successively with 5% aqueous $K_2CO_3$ (2×25 mL) and brine (50 mL), dried ($Na_2SO_4$), and evaporated in vacuo to afford the diamine 15 as a colourless gum (1.30 g).

LC-MS (ESI): $t_R$=4.51 min (m/z=888.8 [M+H]$^+$).

The mixture was stirred at room temperature for 18 h, then filtered to remove the precipitated solids. The residue was re-dissolved in $CH_2C_2$ (10 mL) and filtered twice more. Finally, the solvent was evaporated in vacuo to afford the N-hydroxysuccinimide ester as a white powder.

(Aa)$_x$(PG)$_y$=D-Lys(Boc)$_2$. LC-MS (ESI): $t_R$=3.88 min (m/z=345.1 [M-OSuc]$^+$).
(Aa)$_x$(PG)$_y$=L-Orn(Boc)$_2$. LC-MS (ESI): $t_R$=3.79 min (m/z=331.1 [M-OSuc]$^+$).
(Aa)$_x$(PG)$_y$=L-Ser(O$^t$Bu)(Boc). LC-MS (ESI): $t_R$=3.02 min (m/z=204.1 [M-OSuc]$^+$).
(Aa)$_x$(PG)$_y$=L-Ser(O$^t$Bu)-L-Lys(Boc)$_2$. LC-MS (ESI): $t_R$=3.61 min (m/z=433.1 [M-OSuc]$^+$).
(Aa)$_x$(PG)$_y$=[BocHN(CH$_2$)$_3$]$_2$NCH$_2$CO$_2$H. LC-MS (ESI): $t_R$=3.12 min (m/z=388.1 [M-OSuc]$^+$).

Description 13: General Procedure to Prepare Bis-Oleyl Pentamine Hydrochloride Salts (17; R=Oleyl, m=3, n=4)

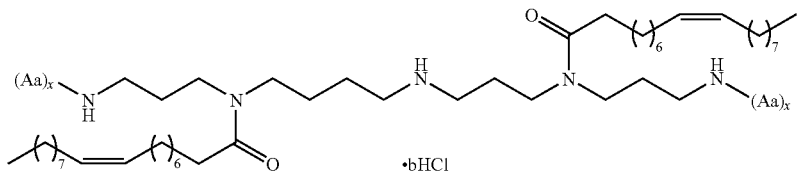

Description 12: General Procedure to Prepare Protected N-Hydroxysuccinimidyl Amino Acids (PG)$_y$ (Aa)$_x$OSuc

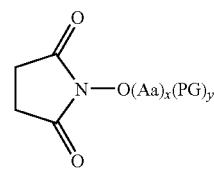

A solution of dicyclohexylcarbodiimide (1.05 eq.) in THF (15 mL) was added at room temperature with stirring to a mixture of N-hydroxysuccinimide (1.1 eq.) and the N-terminal protected amino acid (1 eq.) in anhydrous THF (10 mL).

A solution of the protected N-hydroxysuccinimide amino acid ester (PG)$_y$(Aa)$_x$OSuc (2.2 eq.) and the diamine (1.0 eq.) 15 in THF (30 mM) was treated at room temperature with a solution of $K_2CO_3$ in water (2.2 eq. 0.2M). The mixture was stirred for 18 h and then concentrated in vacuo. The residue was diluted with EtOAc (15 mM), washed with half the same volume of water, dried ($Na_2SO_4$) and the solvent evaporated in vacuo to leave a gum that was purified by column chromatography (silica gel) eluting with a mixture of MeOH and $CHCl_3$ [10:90] to afford the intermediate Boc carbamate 16 as a gum. The gum was treated with a solution of HCl in diethyl ether (2M, 50 mM) at room temperature under nitrogen for 18 h when the precipitated solid was collected by filtration, washed with diethyl ether and dried in vacuo to afford the bis-oleyl pentamine hydrochloride salt 17 as a white powder (66-88% yield).

Example 5
$(Aa)_x$=L-Lys
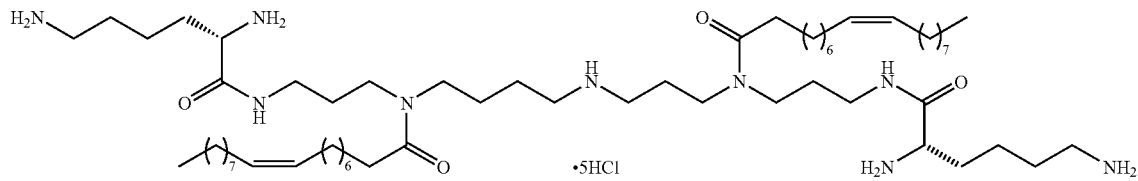
LC-MS (ESI): $t_R$=10.17 min (m/z=1044.96 [M+H]$^+$); HRMS (ESI) m/z calcd ($C_{61}H_{122}N_9O_4$) 1044.9606, found 1044.9626 [M+H]$^+$.
Example 6
$(Aa)_x$=D-Lys
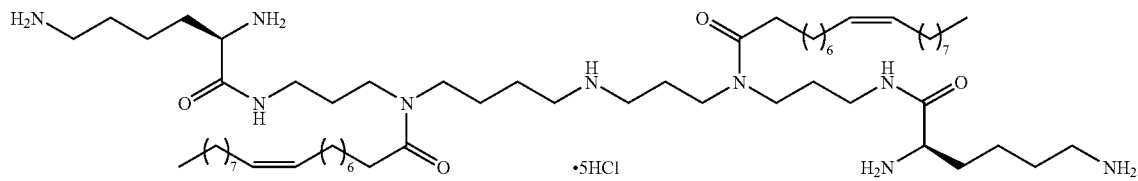
LC-MS (ESI): $t_R$=10.24 min (m/z=1044.96 [M+H]$^+$); HRMS (ESI) m/z calcd ($C_{61}H_{122}N_9O_4$) 1044.9620, found 1044.9630 [M+H]$^+$.
Example 7
$(Aa)_x$=L-Orn
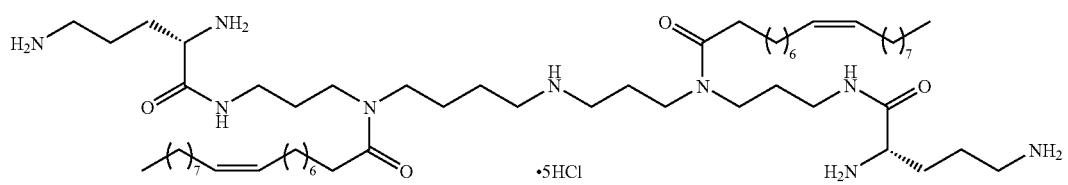
LC-MS (ESI): $t_R$=10.25 min (m/z=1016.93 [M+H]$^+$); HRMS (ESI) m/z calcd ($C_{59}H_{118}N_9O_4$) 1016.9307, found 1016.9313 [M+H]$^+$.

Example 8
$(Aa)_x$=L-Ser
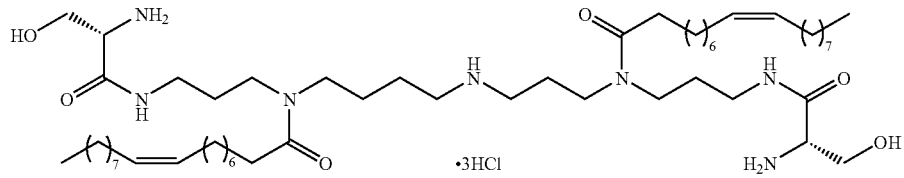
LC-MS (ESI): $t_R$=11.71 min (m/z=962.8364 [M+H]$^+$); HRMS (ESI) m/z calcd ($C_{55}H_{108}N_7O_6$) 962.8361, found 962.8364 [M+H]$^+$.
Example 9
$(Aa)_x$=L-Ser-L-Lys
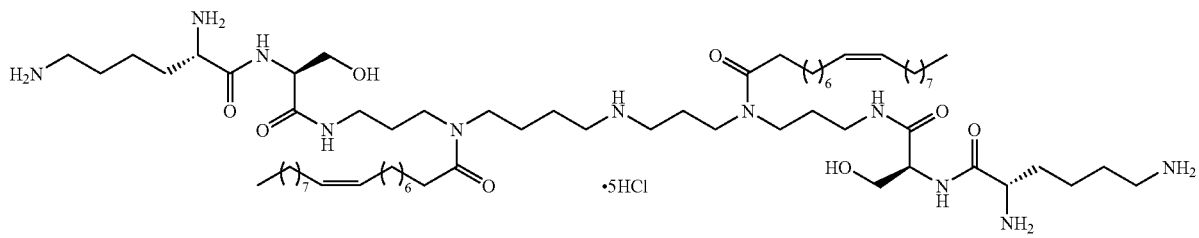
LC-MS (ESI): $t_R$=10.39 min (m/z=1219.03 [M+H]$^+$), HRMS (ESI) m/z calcd ($C_{67}H_{132}N_{11}O_8$) 1219.0260, found 1219.0258 [M+H]$^+$.
Example 10
$(Aa)_x$=[H$_2$N(CH$_2$)$_3$]$_2$NCH$_2$CO$_2$H
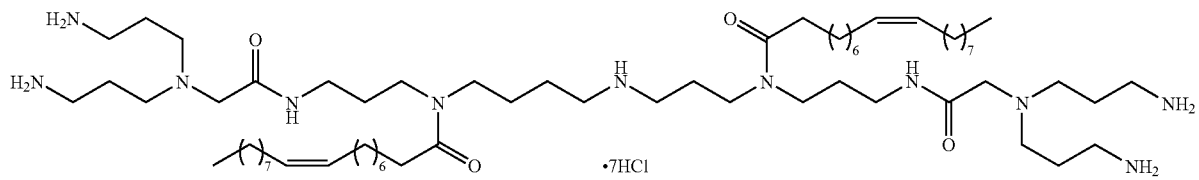
LC-MS (ESI): $t_R$=9.96 min (m/z=1131.05 [M+H]$^+$); HRMS (ESI) m/z calcd ($C_{65}H_{132}N_{11}O_4$) 1131.0464, found 1131.0470 [M+H]$^+$.

Description 14: 2,2,2-Trifluoro-N-[3-(4-{3-[3-(2,2,2-trifluoro-acetylamino)-propylamino]-propylamino}-butylamino)-propyl]-acetamide tris-trifluoroacetic acid salt (18; m=3, n=4)

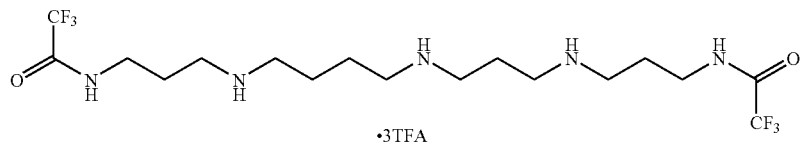

Trifluoroacetic acid (10 mL) was added at room temperature to a stirring solution of the Boc carbamate 13 (4.00 g, 5.14 mmol) in CH$_2$Cl$_2$ (10 mL). After 18 h, the mixture was concentrated in vacuo and the residue was treated with anhydrous diethyl ether (100 mL). The resulting precipitate was collected on a filter and washed with anhydrous diethyl ether (50 mL) to afford the tris-trifluororacetic acid salt 18 as a white powder (4.00 g).

$^1$H-NMR (MeOH): $\delta_H$ 1.75 (m, 4H), 1.95 (m, 4H), 2.10 (m, 2H), 3.05 (m, 8H), 3.15 (m, 4H), 3.38 (m, 4H).

Description 15: Octadec-9-enoic Acid {4-[(3-amino-propyl)-octadec-9-enoyl-amino]-butyl}-{3-[(3-amino-propyl)-octadec-9-enoyl-amino]-propyl}-amide (20; R=oleyl, m=3, n=4)

which was purified by column chromatography (silica gel) eluting with a mixture of MeOH and CHCl$_3$ [3:97] to afford the trifluoroacetamide 19 as a colourless gum.

The gum was dissolved in a mixture of MeOH (10 mL) and water (2 mL) and K$_2$CO$_3$ (1.13 g, 8.12 mmol) was added. This mixture was stirred at room temperature under nitrogen for 18 h and then concentrated in vacuo. The residue was diluted with CH$_2$Cl$_2$ (100 mL) and the organic solution was washed successively with 5% aqueous K$_2$CO$_3$ (2×25 mL) and brine (50 mL), dried (Na$_2$SO$_4$) and evaporated in vacuo to afford the bis-amine 20 as a colourless gum (1.50 g).

LC-MS (ESI): t$_R$=8.98 min (m/z=1053.4 [M+H]$^+$).

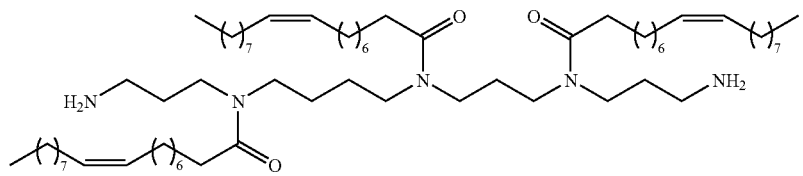

Description 16: General Procedure to Prepare tris-oleyl,bis-(Aa)$_x$-pentamine hydrochloride Salts (22; R=oleyl, m=3, n=4)

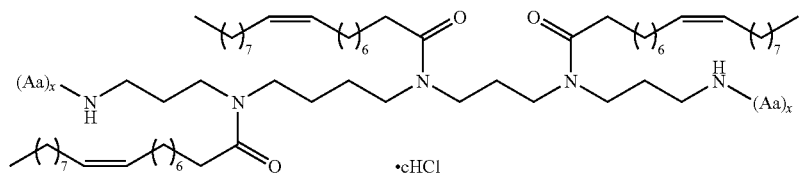

To a solution of oleic acid (3.00 g, 10.6 mmol), 18 (2.50 g, 3.21 mmol) in CH$_2$Cl$_2$ (100 mL) were added TBTU (4.12 g, 12.8 mmol), HOBt (1.73 g, 12.8 mmol) and diisopropylethylamine (4.15 g 32.1 mmol). After stirring at room temperature for 18 h, the mixture was concentrated in vacuo and the residue was re-dissolved in CH$_2$Cl$_2$ (100 mL) and washed successively with 5% aqueous KHSO$_4$ (25 mL), 5% aqueous K$_2$CO$_3$ (2×25 mL), and brine (50 mL). The organic solution was dried (Na$_2$SO$_4$) and concentrated in vacuo to leave an oil A solution of the protected N-hydroxysuccinimide amino acid ester (PG)$_y$(Aa)$_x$OSuc (2.2 eq.) and the diamine (1.0 eq.) 20 in THF (20 mM) was treated at room temperature with a solution of K$_2$CO$_3$ in water (2.2 eq. 0.2M). The mixture was stirred for 18 h under nitrogen and then concentrated in vacuo. The residue was diluted with EtOAc (10 mM), washed with half the same volume of water, dried (Na$_2$SO$_4$) and the solvent evaporated in vacuo to leave a gum that was purified by column chromatography (silica gel) eluting with a mixture of MeOH and CHCl₃ [10:90] to afford the intermediate Boc carbamate 21 as a gum. The gum was treated with a solution of HCl in diethyl ether (2M, 50 mM) at room temperature under nitrogen for 18 h and the precipitated solid was collected by filtration, washed with anhydrous diethyl ether and dried in vacuo to afford the tris-oleyl pentamine hydrochloride salt 22 as a white powder (41-56% yield).

Example 11

$(Aa)_x$=L-Lys

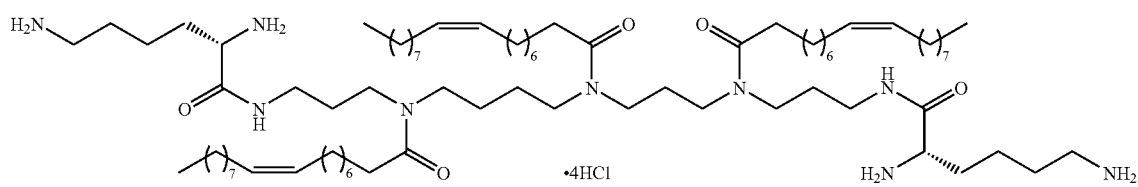

LC-MS (ESI): $t_R$=12.94 min (m/z=1309.20 [M+H]$^+$); HRMS (ESI) m/z calcd ($C_{79}H_{154}N_9O_5$) 1309.2073, found 1309.2070 [M+H]$^+$.

Example 12

$(Aa)_x$=D-Lys

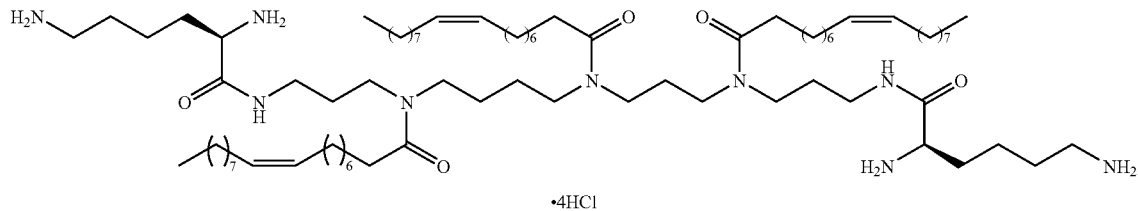

LC-MS (ESI): $t_R$=12.94 min (m/z 1309.20 [M+H]$^+$); HRMS (ESI) m/z calcd ($C_{79}H_{154}N_9O_5$) 1309.2073, found 1309.2075 [M+H]$^+$.

Example 13

$(Aa)_x$=L-Orn

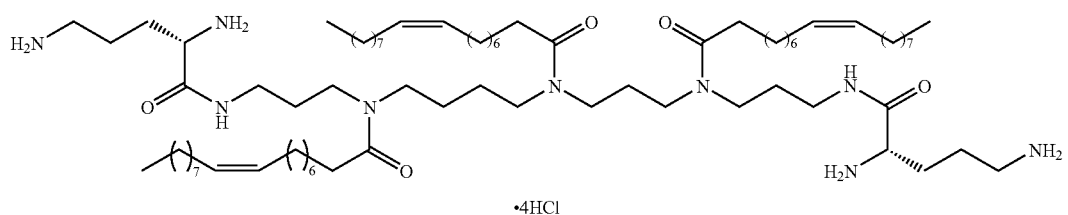

LC-MS (ESI): $t_R$=12.97 min (m/z=1281.17 [M+H]$^+$); HRMS (ESI) m/z calcd ($C_{59}H_{118}N_9O_5$) 1281.1760, found 1281.1759 [M+H]$^+$.

Example 14
$(Aa)_x$=L-Ser
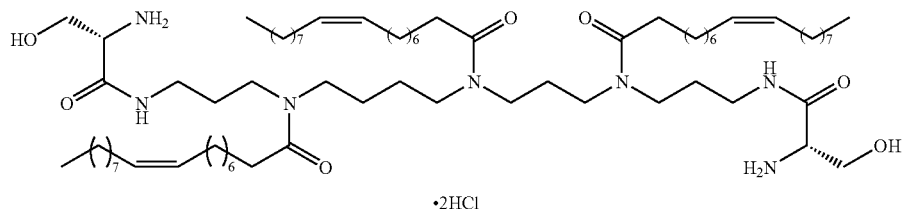
LC-MS (ESI): $t_R$=17.28 min (m/z=1227.08 [M+H]$^+$); HRMS (ESI) m/z calcd ($C_{73}H_{140}N_7O_7$) 1227.0814, found 1227.0814 [M+H]$^+$.
Example 15
$(Aa)_x$=L-Ser-L-Lys
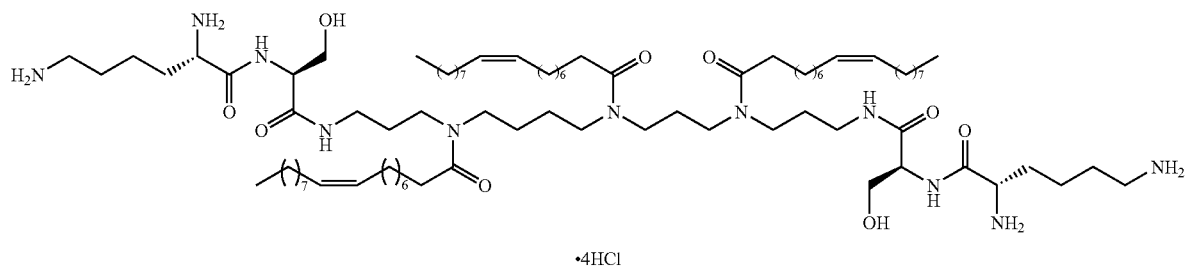
LC-MS (LC-TOF): $t_R$=3.17 min (1484.60 [M+H]$^+$).
Example 16
$(Aa)_x$=[$H_2N(CH_2)_3$]$_2NCH_2CO_2H$
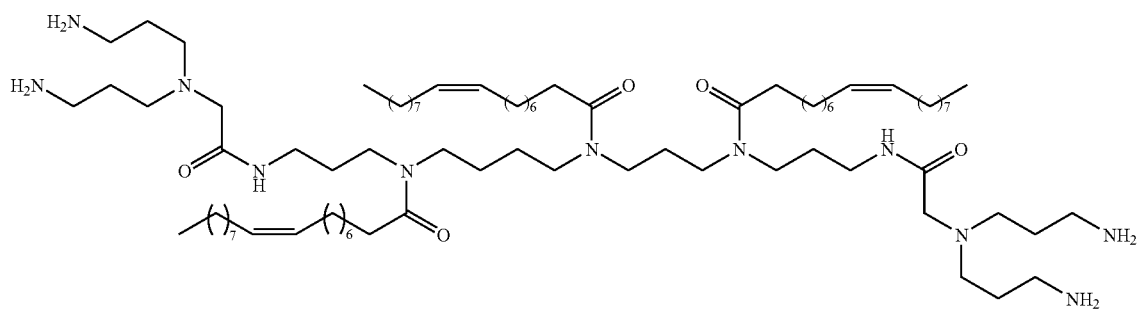
LC-MS (LC-TOF): $t_R$=3.83 min (m/z=1396.75 [M+H]$^+$).

Example 17

Preparation of Bis-Oleyl Pentamine Hydrochloride Salt (23; R=Oleyl, M=3, N=4)

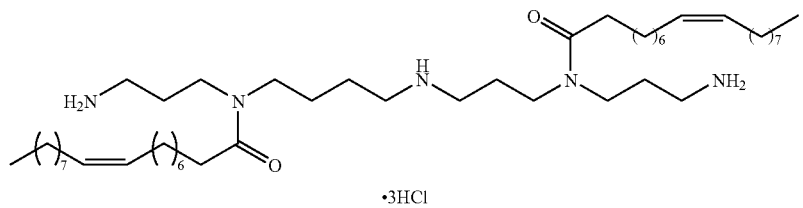

•3HCl

The mono-Boc diamine 14 (90.0 mg, 0.10 mmol) was treated with a solution of HCl in diethyl ether (2M, 5 mL) and stirred at room temperature under nitrogen for 3 h. The solvent was evaporated under a stream of nitrogen and the residual solid was washed with anhydrous diethyl ether (2 mL) and dried in vacuo to afford the tris-hydrochloride salt 23 as a white powder (85.0 mg).

LC-MS (ESI): $t_R$=12.28 min (m/z=788.77 [M+H]$^+$); HRMS (ESI) m/z calcd ($C_{49}H_{98}N_5O_2$) 788.7721, found 788.7710 [M+H]$^+$.

Example 18

Preparation of tris-oleyl pentamine hydrochloride Salt (24; R=oleyl, m=3, n=4)

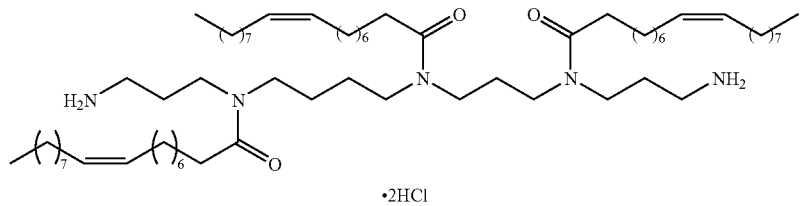

•2HCl

The tris-oleate 20 (85.0 mg, 81.0 μmol) was treated with a solution of HCl in diethyl ether (1.5M, 5 mL) and stirred at room temperature under nitrogen for 3 h. The solvent was evaporated under a stream of nitrogen and the residual white solid was washed with anhydrous diethyl ether (2 mL) and dried in vacuo to afford the bis-hydrochloride salt 24 as a white powder (70.0 mg).

LC-MS (ESI): $t_R$=17.63 min (m/z=1053.01 [M+H]$^+$); HRMS (ESI) m/z calcd ($C_{67}H_{130}N_5O_3$) 1053.0174, found 1053.0181 [M+H]$^+$.

Example 19

Transfection of Recombinant Plasmid Expressing GFP into Cells Using Pentamine-Based Compounds Transfection studies were performed using the adherent cell line CHO-K1, CV1 and A549 cells. Complete medium consisted of F12 (for CHO-K1), and DMEM (for CV1, A549) medium supplemented with 10% v/v foetal bovine serum and 1×L-Glutamine. All media and supplements were obtained from Life Technologies.

In Vitro Gene Transfection

Cells were seeded into tissue culture treated 96-well plates (Costar) 16-18 hours prior to transfection at an approximate density of 2×10$^4$ cells/well. A 0.025 μg/μl plasmid solution was prepared in Optimem. The plasmid used was pCMV-eGFP obtained from Clontech. The pentamine lipid was dissolved in Optimem as a 10× concentrate so as to achieve a final concentration of 20, 10, 5 and 2.5 μg/ml in final the reaction mixture. 10 μl of the pentamine lipid was mixed with 10 μl of the plasmid for each well. The complex was incubated at room temperature for 10 minutes. The medium was removed from the cells in the plate and they were washed once with 100 μl PBS. The complex (20 μl) was added to each well and then 80 μl Optimem (serum-free) or growth medium (serum) was added to make a final volume of 100 μl. In the serum-free protocol, the plate was then incubated for 6 hours at 37° C. and the medium was then removed and fresh complete medium was added to each well and incubation continued for a further 18 hours. In the serum protocol, the plate was incubated for 24 h at 37° C.

Reporter gene assays were performed according to the manufacturer's guidelines (Roche Diagnostics). The medium was removed from the plate and the cells were washed once with 100 μl PBS. 100 μl reporter lysis buffer (50 mM HEPES pH 7.5, 2 mM EDTA, 0.05% triton×100, 2 mM DTT) was then added to each well. The plate was then placed at −80° C. for 15 min subsequently allowed to thaw at room temperature. Fluorescence was then measured using a standard plate reader (Tecan Ultra, Tecan) with excitation wavelength 485 nm and emission wavelength 520 nm.

FIG. 8 shows the expression of GFP in CHO-K1 cells that have been transfected with the aid of the compound of Example 4.

FIG. 9 shows the expression of pCMV-eGFP in A549 cells that have been transfected with the aid of the compound of Examples 12, 13, 15, 17 and 18.

FIG. 10 shows the expression of pCMV-eGFP in CV-1 cells that have been transfected with the aid of the compound of Examples 5, 6, 7, 8 and 11.

FIG. 11 shows the expression of pCMV-eGFP in CV-1 cells that have been transfected with the aid of the compound of Examples 12, 13, 15, 17 and 18.

Example 20

Transfection of siRNA into Cells Using Pentamine-Based Surfactant Compounds

Knockdown studies were performed using the adherent cell lines A549, Ishikawa, MCF7 and Caco2. Complete medium consisted DMEM (for A549, Ishikawa, MCF7) and EMEM (for Caco2) medium supplemented with 10% v/v foetal bovine serum and 1×L-Glutamine. All media and supplements were obtained from Life Technologies.

In Vitro siRNA Transfection

Cells were seeded into tissue culture treated 96-well plates (Costar) 16-18 hours prior to transfection at an approximate density of $2 \times 10^4$ cells/well. A 1 uM solution of siRNA (targeting JNK1 or non-targeting control) purchased from Dharmacon was prepared in Optimem. The Gemini lipid was dissolved in Optimem as a 10× concentrate so as to achieve a final concentration of 5 µg/ml in final the reaction mixture. The commercial reagent lipofectamine 2000 was used at a final concentration of 2.5 µg/ml. A 10 ul sample of the Gemini lipid was mixed with 10 ul of the siRNA for each well. The complex was incubated at room temperature for 10 minutes. The medium was removed from the cells in the plate and they were washed once with 100 µl PBS. The complex (20 µl) was added to each well and then 80 µl growth medium (serum) was added to make a final volume of 100 µl. and the plate was incubated for 24 h at 37° C. At this time point the cells were washed once using 100 µl PBS and then lysed in 100 µl RNA lysis buffer (Promega). Standard quantitative RT-PCR (taqman) was carried out to determine the relative abundance of Jnk1 compared to the housekeeping gene GAPDH in both Jnk1 siRNA targeted and non-targeted cells. The degree of knockdown was expressed as a ratio of treated (Jnk1) copies of Jnk1 to control (non-targeted) copies of Jnk1.

FIG. 12 shows the knockdown of Jnk1 in Caco2 cells that have been transfected with the aid of the compound of Examples 12, 13 and 4.

FIG. 13 shows the knockdown of Jnk1 in Ishikawa cells that have been transfected with the aid of the compound of Example 13.

FIG. 14 shows the knockdown of Jnk1 in MCF7 cells that have been transfected with the aid of the compound of Example 13.

FIG. 15 shows the knockdown of Jnk1 in A549 cells that have been transfected with the aid of the compound of Examples 12 and 13.

All publications, including but not limited to patents and patent applications, cited in this specification are herein incorporated by reference as if each individual publication were specifically and individually indicated to be incorporated by reference herein as though fully set forth.

Figure 1:
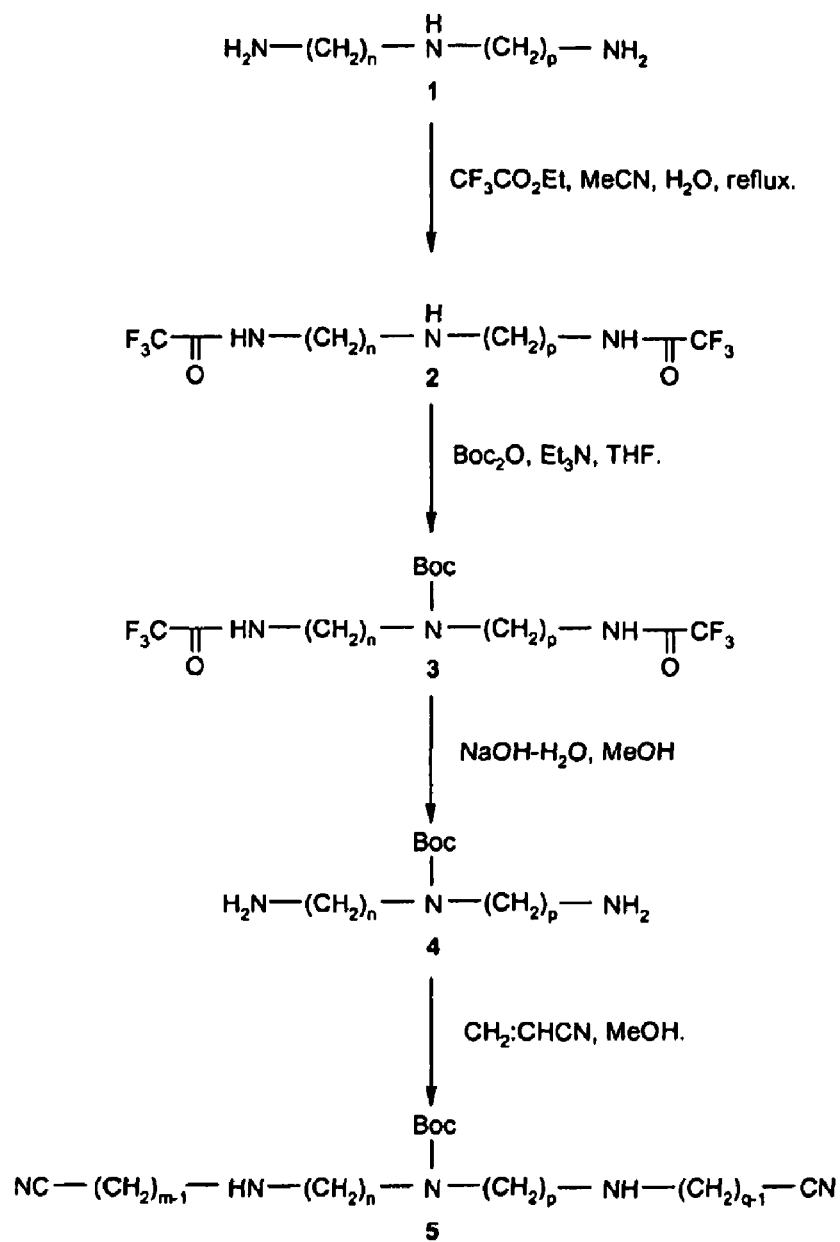
FIG. 1 shows a general scheme for the synthesis of an advanced intermediate 5 useful in the synthesis of molecules of the invention
Figure 2:
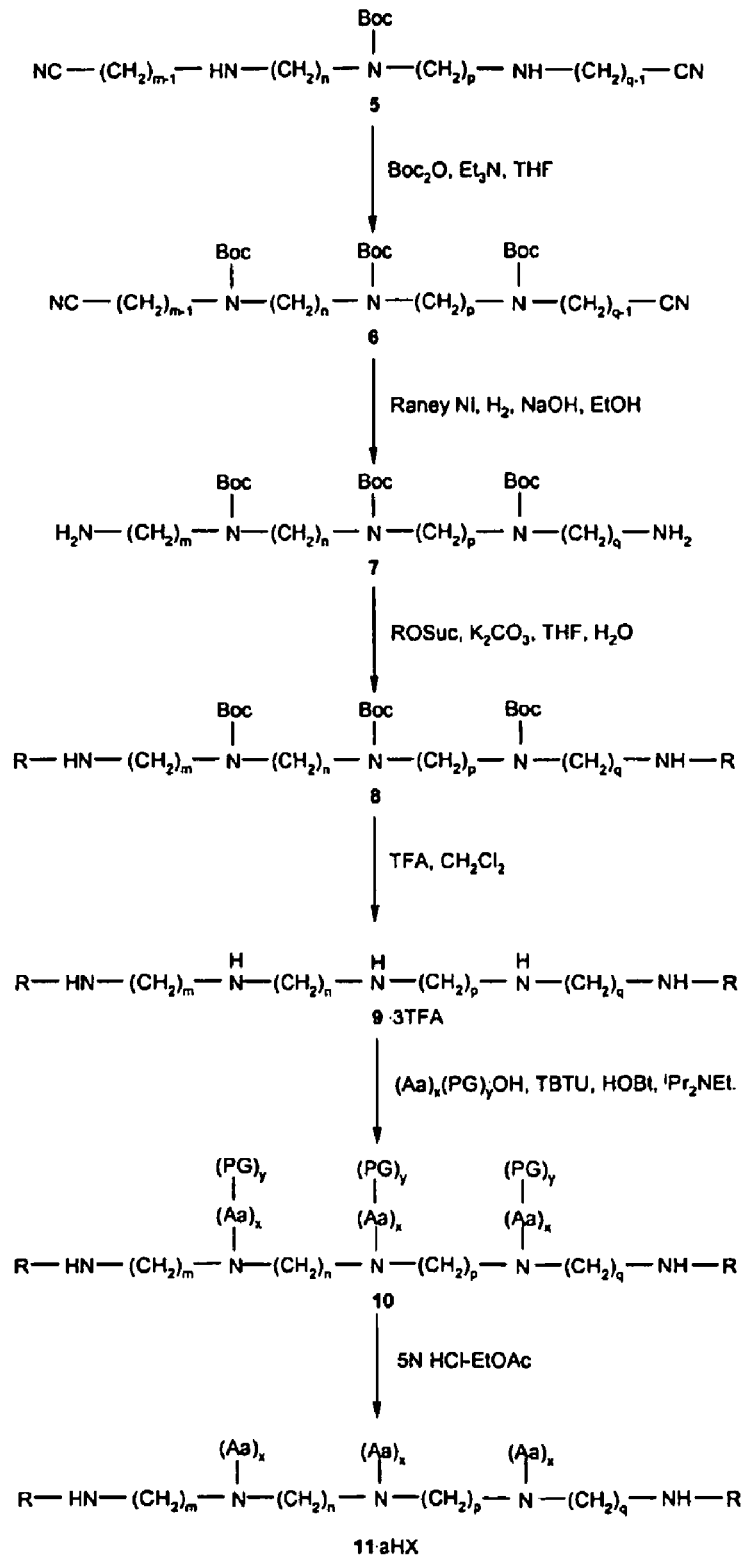
FIG. 2 shows a general scheme for the synthesis of molecules according to one general embodiment of the invention.
Figure 3:
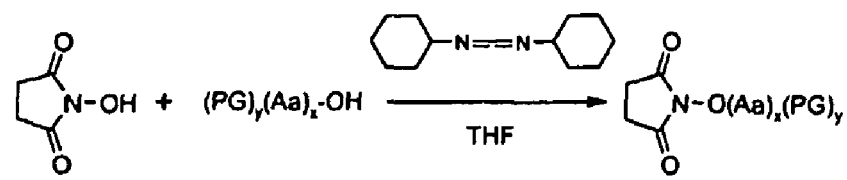
FIG. 3 shows a reaction scheme for the preparation of an activated amino acid $(Aa)_x$ group useful in the synthesis of molecules according to the invention.
Figure 4:
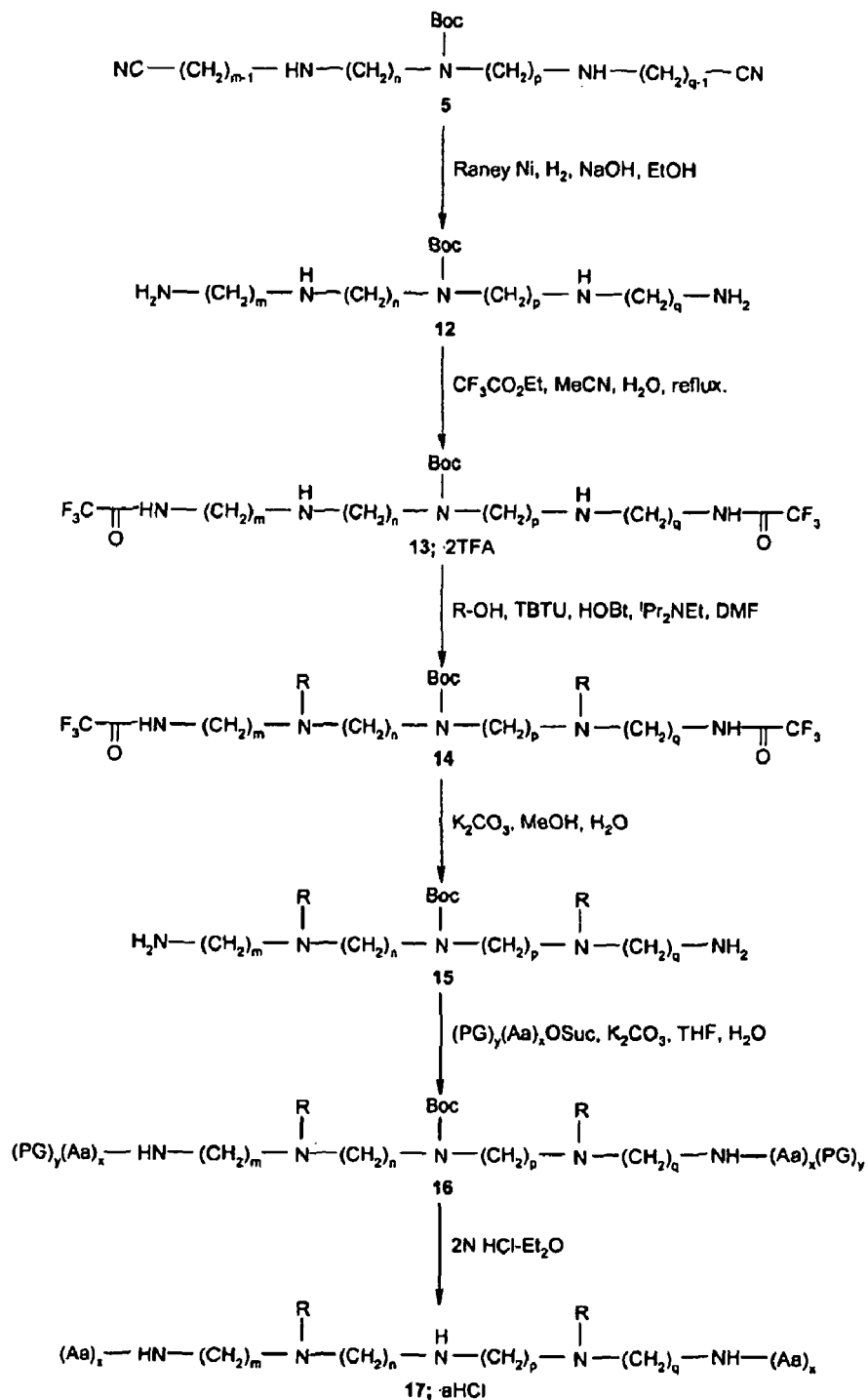
FIG. 4 shows a general scheme for the synthesis of molecules according to a further general embodiment of the invention.
Figure 5:
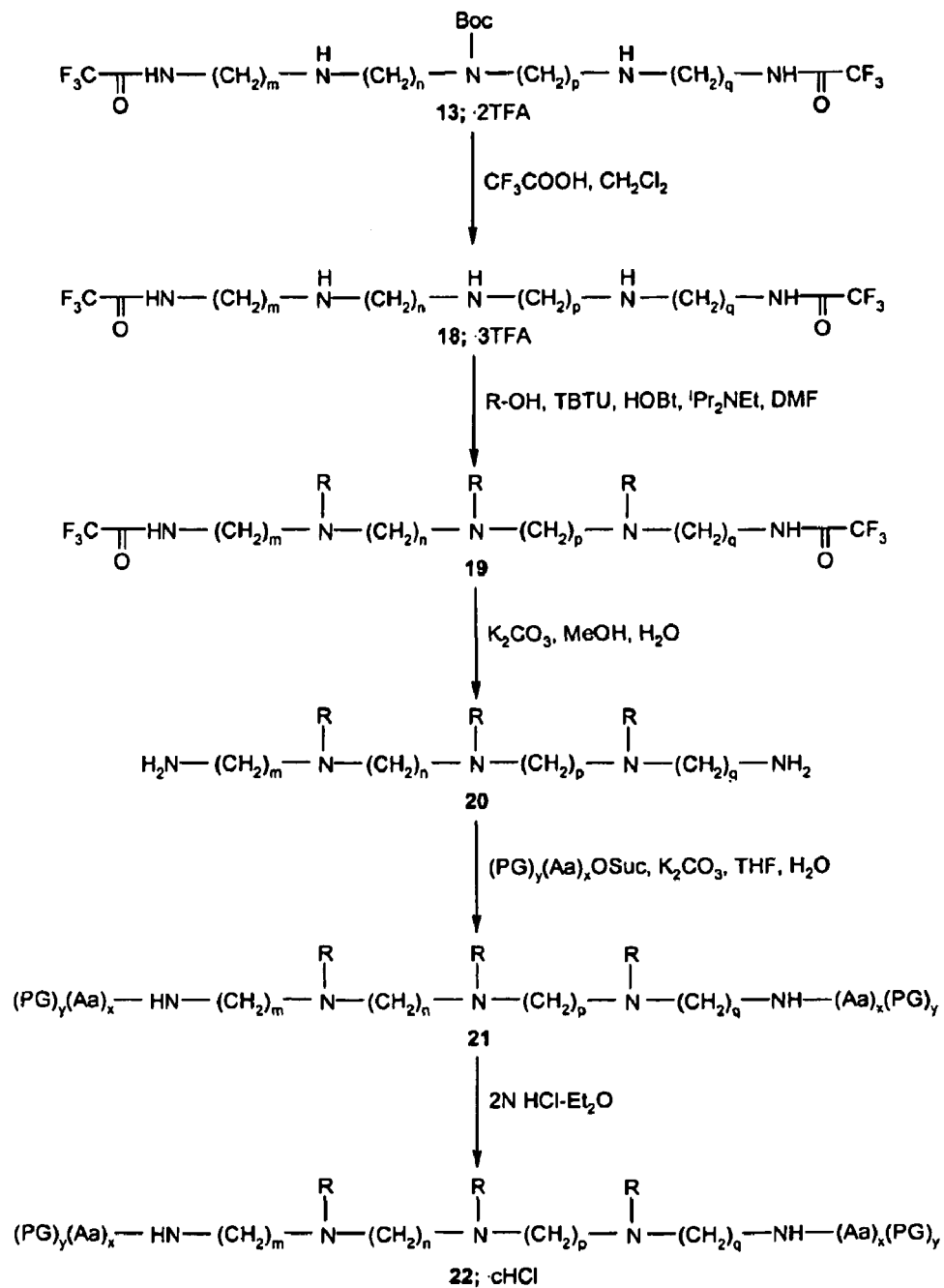
FIG. 5 shows a general scheme for the synthesis of molecules according to a further general embodiment of the invention.
Figure 6:
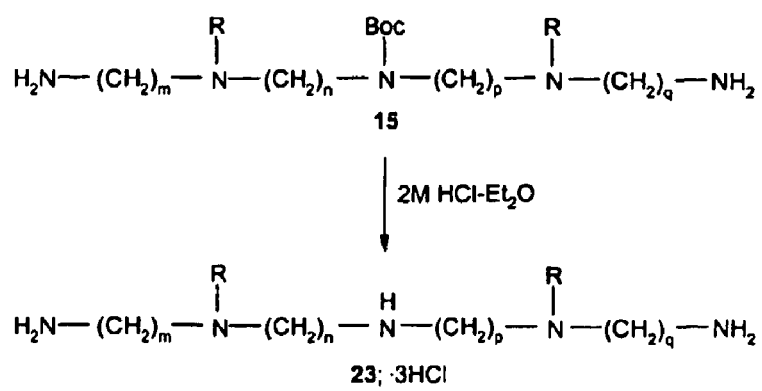
FIG. 6 shows a general reaction scheme for the deprotection of an advanced intermediate for the generation of a salt of a molecule according to one embodiment of the invention.
Figure 7:
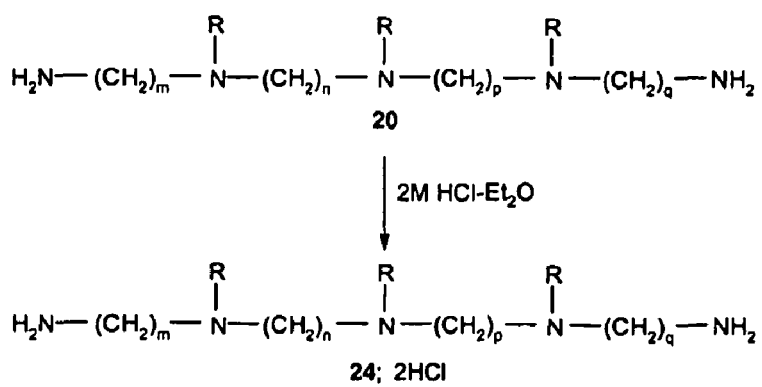
FIG. 7 shows a reaction scheme for the generation of a salt according to one embodiment of the invention.
Figure 8:
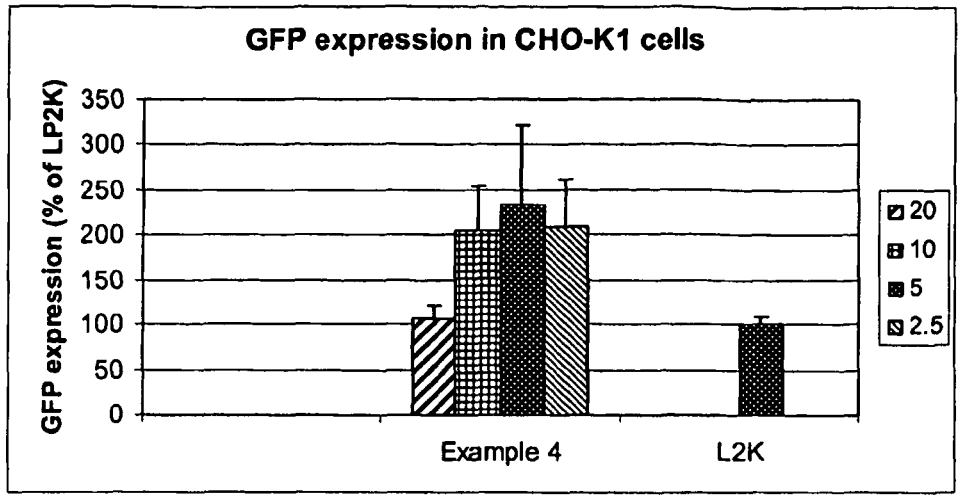
FIG. 8 shows the expression of GFP in CHO-K1 cells that have been transfected with the aid of the compound of Example 4. Concentrations of example 4 are given in ug/mi. L2K denotes lipofectamine 2000™.
Figure 9:
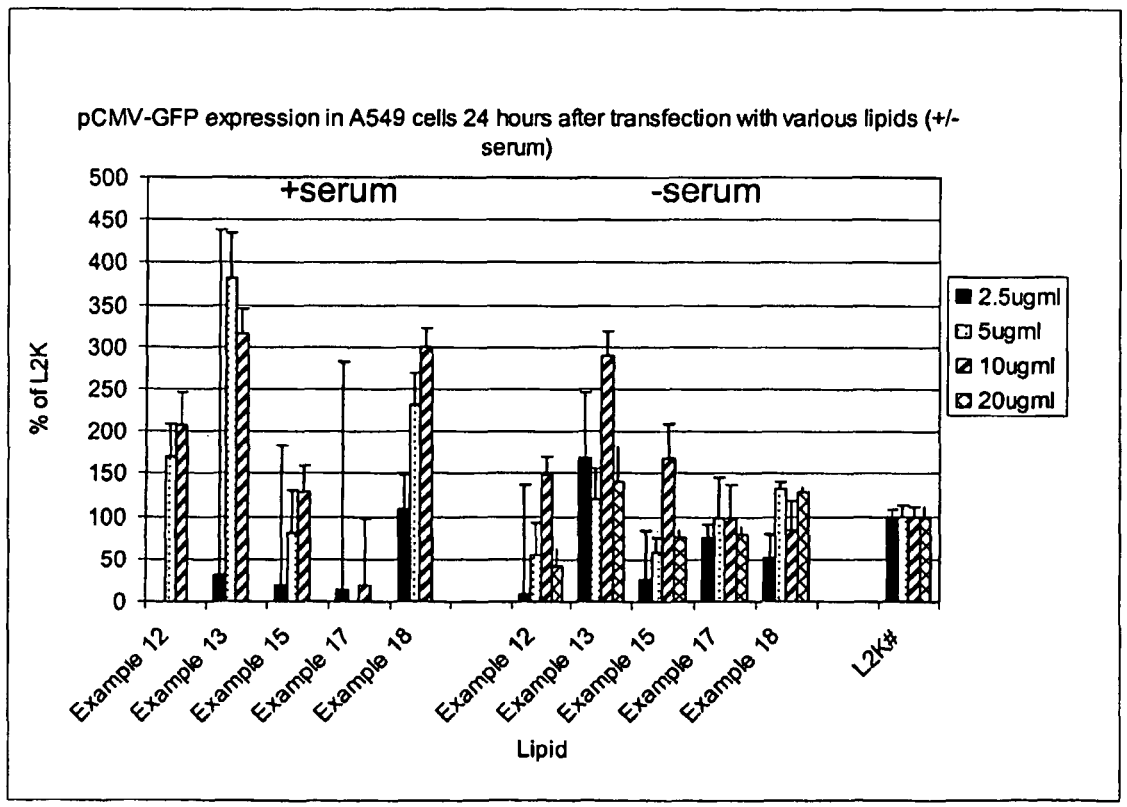
FIG. 9 shows the expression of pCMV-GFP in A549 cells that have been transfected with the aid of the compound of Examples 12, 13, 15, 17 and 18. L2K# denotes lipofectamine 2000™.
Figure 10:
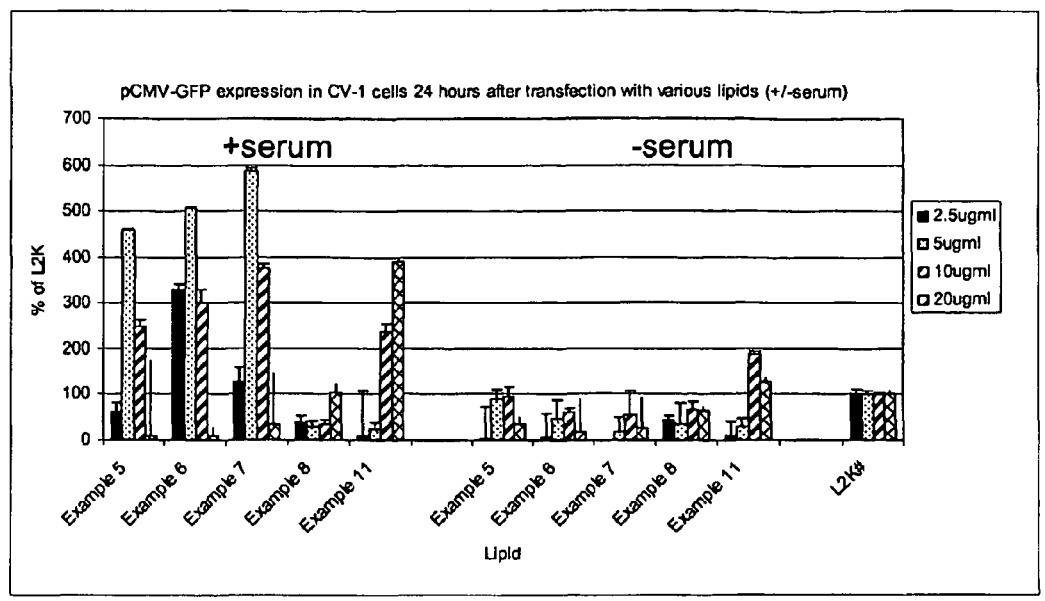
FIG. 10 shows the expression of pCMV-GFP in CV-1 cells that have been transfected with the aid of the compound of Examples 5, 6, 7, 8 and 11. L2K# denotes lipofectamine 2000™.
Figure 11:
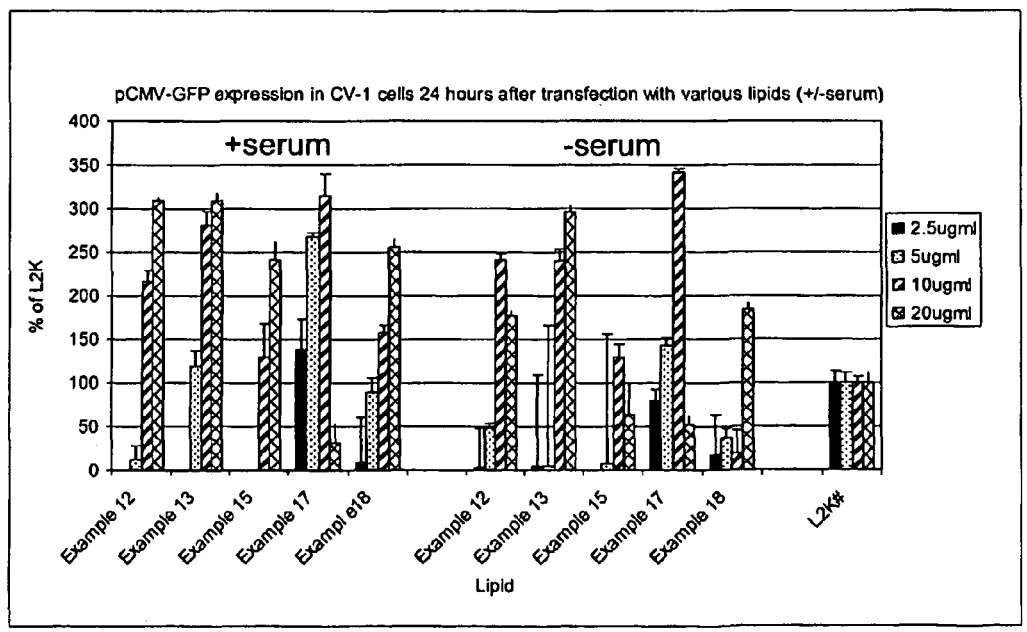
FIG. 11 shows the expression of pCMV-GFP in CV-1 cells that have been transfected with the aid of the compound of Examples 12, 13, 15, 17 and 18. L2K# denotes lipofectamine 2000™.
Figure 12:
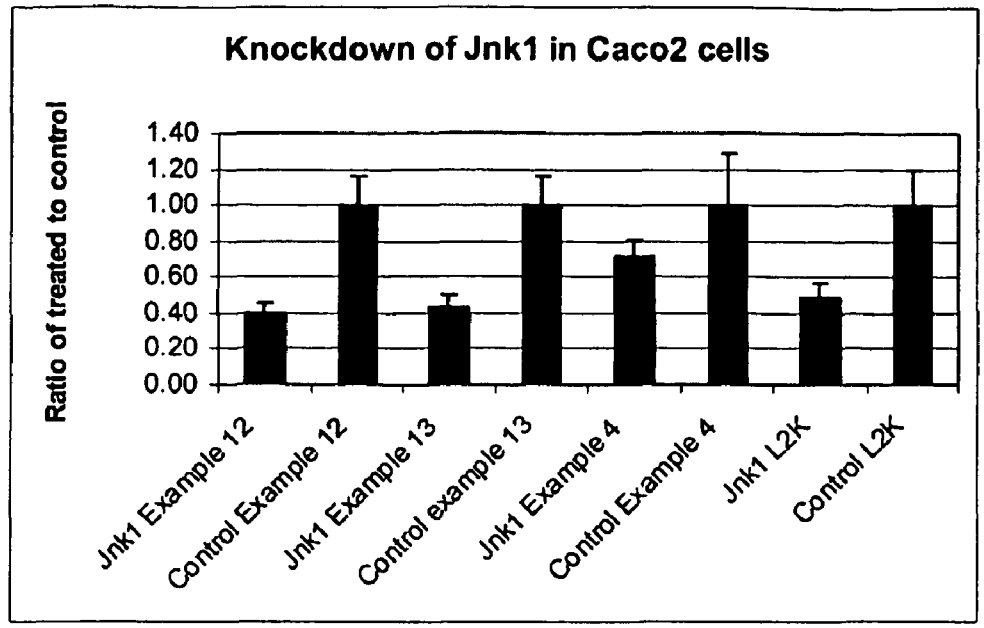
FIG. 12 shows the knockdown of Jnk1 in Caco2 cells that have been transfected with the aid of the compound of Examples 12, 13 and 4. L2K denotes lipofectamine 2000™.
Figure 13:
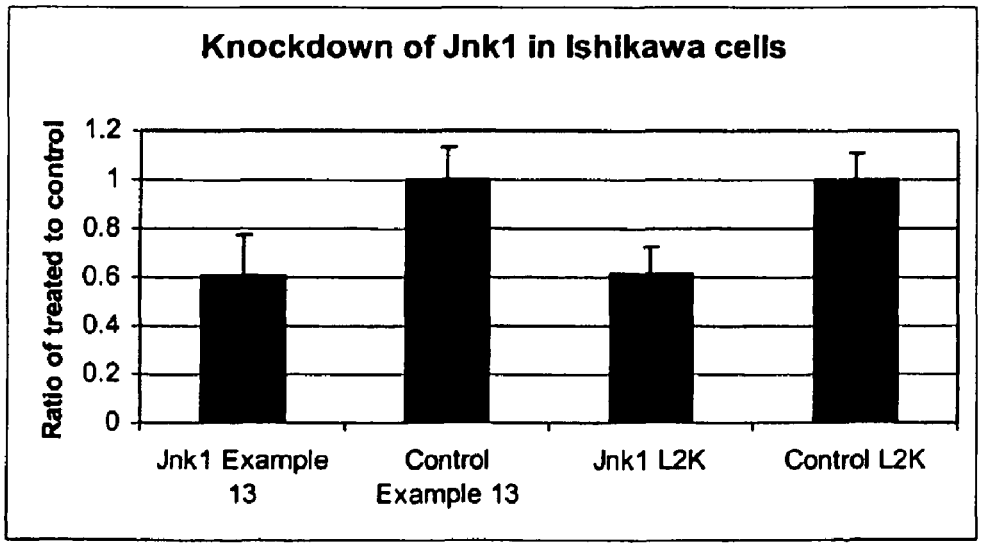
FIG. 13 shows the knockdown of Jnk1 in Ishikawa cells that have been transfected with the aid of the compound of Example 13. L2K denotes lipofectamine 2000™.
Figure 14:
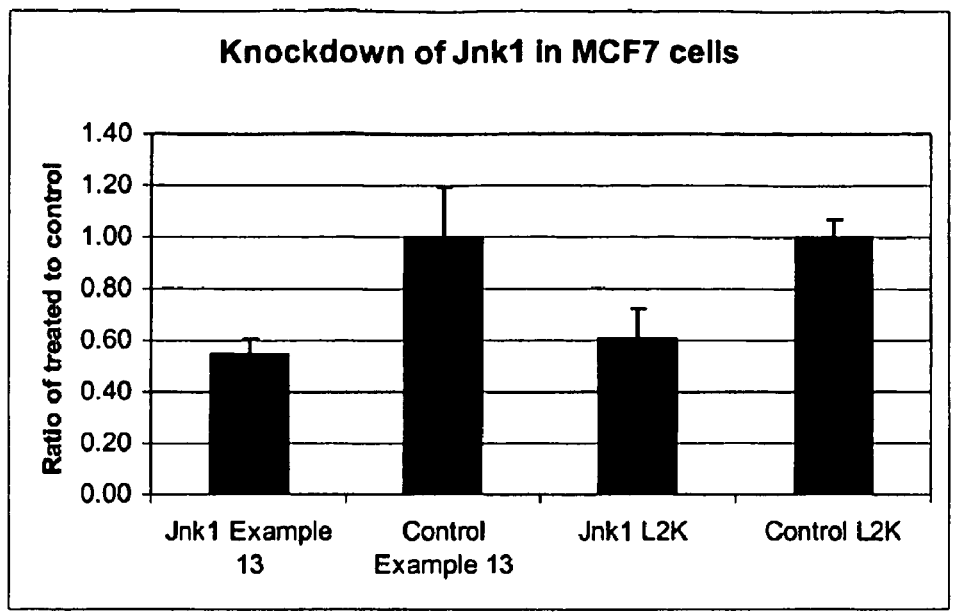
FIG. 14 shows the knockdown of Jnk1 in MCF7 cells that have been transfected with the aid of the compound of Example 13. L2K denotes lipofectamine 2000™.
Figure 15:
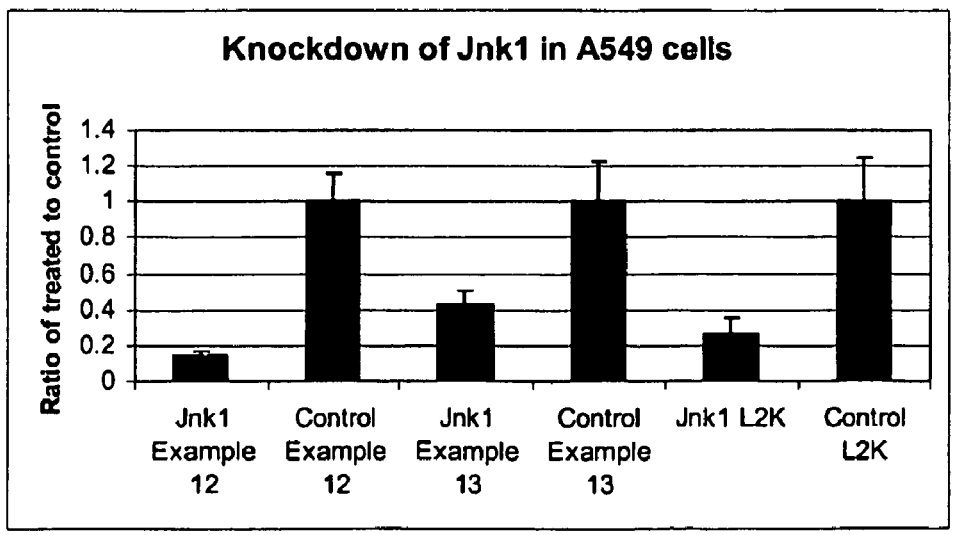
FIG. 15 shows the knockdown of Jnk1 in A549 cells that have been transfected with the aid of the compound of Examples 12 and 13. L2K denotes lipofectamine 2000™.

The invention claimed is:

1. A compound having the general structure of formula (I):

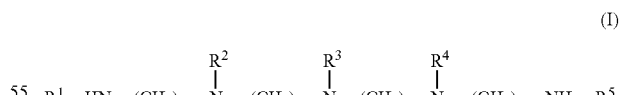

(I)

wherein m is 1 to 6;

q is 1 to 6;

n is 1 to 10;

p is 1 to 10;

$R^1$ and $R^5$ are each independently $R^w$, and $R^2$, $R^3$ and $R^4$ are each independently $(Aa)_x$; or $R^2$ and $R^4$ are each independently $R^w$, $R^3$ is H and $R^1$ and $R^5$ are each independently $(Aa)_x$; or R² and R⁴ are each independently R^w, and R¹, R³ and R⁵ are each independently (Aa)ₓ; or R², R³ and R⁴ are each independently R^w and R¹ and R⁵ are each independently (Aa)ₓ;

where R^w is a saturated or unsaturated, branched or unbranched aliphatic carboxylic acid of up to 24 carbon atoms linked as its amide derivative;

Aa, which may be the same or different at each occurrence, is [H₂N(CH₂)₃]N(CH₂)CO—, or (H₂NCH₂)₂CHCO—, or an enantiomer of HOCH₂CH(NH₂)C(O)—, NH₂(CH₂)₄CH(NH₂)C(O)—, NH₂(CH₂)₃CH(NH₂)C(O)—, NH₂CH₂CH₂CH(NH₂)C(O)—, NH₂CH₂CH(NH₂)C(O)—, or H₂N(CH₂)₄CH(NH₂)C(O)NHCH(CH₂OH)C(O)—; and x is 1;

or a pharmaceutically acceptable salt thereof.

2. A compound according to claim 1 in which m is 2 or 3.

3. A compound according to claim 2 in which q is 2 or 3.

4. A compound according to claim 3 in which n is 3 to 6.

5. A compound according to claim 1 in which p is 3 to 6.

6. A compound according to claim 1 in which R¹ and R⁵ are each independently R^w, and R², R³ and R⁴ are each independently (Aa)ₓ.

7. A compound according to claim 1 in which R² and R⁴ are each independently R^w, R³ is hydrogen, and R¹ and R⁵ are each independently (Aa)ₓ.

8. A compound according to claim 1 in which R² and R⁴ are each independently R^w, and R¹, R³ and R⁵ are each independently (Aa)ₓ.

9. A compound according to claim 1 in which R², R³ and R⁴ are each independently R^w; and R¹ and R⁵ are each independently (Aa)ₓ.

10. A compound according to claim 1 in which the R^w saturated or unsaturated, branched or unbranched aliphatic carboxylic acid of up to 24 carbon atoms linked as its amide derivative has 12 or more carbon atoms.

11. A compound according to claim 1 in which the R^w saturated or unsaturated, branched or unbranched aliphatic carboxylic acid of up to 24 carbon atoms linked as its amide derivative is:

—C(O)(CH₂)₁₀CH₃
—C(O)(CH₂)₁₂CH₃
—C(O)(CH₂)₁₄CH₃
—C(O)(CH₂)₁₆CH₃
—C(O)(CH₂)₁₈CH₃
—C(O)(CH₂)₂₀CH₃
—C(O)(CH₂)₇CH=CH(CH₂)₅CH₃ natural mixture
—C(O)(CH₂)₇CH=CH(CH₂)₇CH₃ natural mixture
—C(O)(CH₂)₇CH=CH(CH₂)₅CH₃ Cis
—C(O)(CH₂)₇CH=CH(CH₂)₇CH₃ Cis
—C(O)(CH₂)₇CH=CH(CH₂)₅CH₃ Trans
—C(O)(CH₂)₇CH=CH(CH₂)₇CH₃ Trans
—C(O)(CH₂)₇CH=CHCH₂CH=CH(CH₂)₄CH₃
—C(O)(CH₂)₇(CH=CHCH₂)₃CH₃
—C(O)(CH₂)₃CH=CH(CH₂CH=CH)₃CH₂)₄CH₃
—C(O)(CH₂)₇CHCH(CH₂)₇CH₃
—C(O)CH₂CH(CH₃)[CH₂CH₂CH₂CH(CH₃)]₃CH₃
or —C(O)(CH₂)₂₂CH₃.

12. The compound of formula:

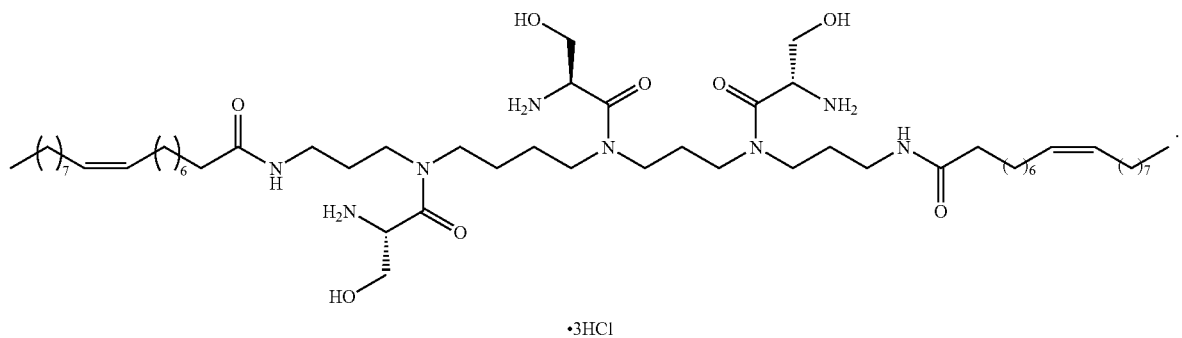

·3HCl

13. The compound of formula:

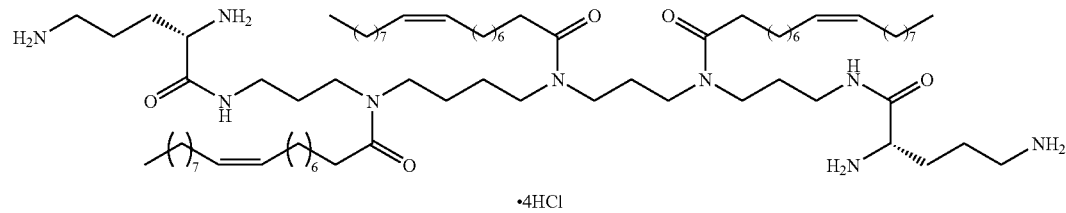

·4HCl